United States Patent [19]
Song et al.

[11] Patent Number: 6,037,488
[45] Date of Patent: Mar. 14, 2000

[54] TRISUBSTITUTED PHENYL DERIVATIVES HAVING RETINOID AGONIST, ANTAGONIST OR INVERSE AGONIST TYPE BIOLOGICAL ACTIVITY

[75] Inventors: Tae K. Song, Long Beach; Min Teng, Aliso Viejo; Roshantha A. Chandraratna, Mission Viejo, all of Calif.

[73] Assignee: Allergan Sales, Inc., Irvine, Calif.

[21] Appl. No.: 08/845,019

[22] Filed: Apr. 19, 1997

[51] Int. Cl.[7] .................................................. C07C 69/76
[52] U.S. Cl. ............................ 560/52; 560/57; 560/101; 562/460; 562/463; 562/491
[58] Field of Search ................................. 560/52, 57, 101; 562/460, 463, 491

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. ........................ 252/299.26 |
| 4,539,154 | 9/1985 | Krebs ....................................... 260/410 |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,826,984 | 5/1989 | Berlin et al. ............................ 546/134 |
| 4,855,320 | 8/1989 | Chatterjee et al. . |
| 4,895,868 | 1/1990 | Chandraratna . |
| 4,923,884 | 5/1990 | Chandraratna ........................... 514/354 |
| 4,927,947 | 5/1990 | Chandraratna ........................... 549/484 |
| 4,980,369 | 12/1990 | Chandraratna . |
| 4,992,468 | 2/1991 | Chandraratna . |
| 5,006,550 | 4/1991 | Chandraratna . |
| 5,013,744 | 5/1991 | Chandraratna . |
| 5,015,658 | 5/1991 | Chandraratna . |
| 5,023,341 | 6/1991 | Chandraratna . |
| 5,037,825 | 8/1991 | Klaus et al. .......................... 514/233.8 |
| 5,045,551 | 9/1991 | Chandraratna . |
| 5,053,523 | 10/1991 | Chandraratna . |
| 5,068,252 | 11/1991 | Chandraratna . |

(List continued on next page.)

FOREIGN PATENT DOCUMENTS

| | | |
|---|---|---|
| 170105A | of 0000 | European Pat. Off. . |
| 0098591 | 1/1984 | European Pat. Off. . |
| 0130795 | 1/1985 | European Pat. Off. ...... C07D 311/58 |
| 0176032 | 4/1986 | European Pat. Off. ........ C07C 65/38 |
| 0176033 | 4/1986 | European Pat. Off. ...... C07D 261/18 |
| 0253302 | 1/1988 | European Pat. Off. ...... C07D 213/16 |
| 0272921 | 6/1988 | European Pat. Off. . |
| 0284261 | 9/1988 | European Pat. Off. ...... C07D 213/80 |
| 0284288 | 9/1988 | European Pat. Off. ...... C07D 401/04 |
| 0286364 | 10/1988 | European Pat. Off. . |
| 0303186 | 2/1989 | European Pat. Off. . |
| 0303915 | 2/1989 | European Pat. Off. ...... A61K 31/255 |
| 176034A | 4/1989 | European Pat. Off. ........ C07C 63/66 |
| 0315071 | 5/1989 | European Pat. Off. ........ C07C 63/66 |
| 0350846 | 7/1989 | European Pat. Off. ...... C07D 311/85 |
| 0412387 | 2/1991 | European Pat. Off. . |
| 0478787 | 10/1991 | European Pat. Off. . |
| 0514269 | 11/1992 | European Pat. Off. . |
| 0617020 | 9/1994 | European Pat. Off. . |
| 0619116 | 10/1994 | European Pat. Off. . |
| 0661259 | 5/1995 | European Pat. Off. ...... C07C 233/81 |
| 0661258 | 7/1995 | European Pat. Off. . |
| 0661261 | 7/1995 | European Pat. Off. . |
| 0718285 | 8/1996 | European Pat. Off. . |
| 3316932 | 11/1983 | Germany ....................... C07C 63/66 |

(List continued on next page.)

OTHER PUBLICATIONS

Chem. Abst. 101:15461 (1984).
A General Synthesis of Terminal and Internal Arylalkynes by the Palladium–Catalyzed Reaction of Alkynylzinc Reagents with Aryl Halides by Anthony O. King and Ei–i–chi, *J. Org. Chem.*, (1978) 43/2: p. 358.
Conversion of Methyl Ketones into Terminal Acetylenes and (E)–Tri–substituted Olefins of Terpenoid Origin by Ei–ichi, et al., *J. Org. Chem.*, (1980) 45/12: p. 2526.
Sporn et al. in *J. Amer. Acad. Derm* . . . (1986) 15:756–764.
"A Convenient Synthesis of Ethynylarenes and Diethynylarenes" by S. Takahashi et al. *Synthesis* (1980) p.627–630.
Shudo et al. in *Chem. Phar. Bull.*, (1985) 33:404–407.
Kagechika et al. in *J. Med. Chem.*, (1988) 31:2182–2192.
Chemistry and Biology of Synthetic Retinoids by Marcia I. Dawson and William II. Okamura, published by CRC Press Inc., 1990, p.334–335, 354.
Synthesis of 2.2'–Diacyl–1,1'–Biaryls. Regiocontrolled Protection of . . . by Mervic, et al, *J. Org. Chem.*, (1980) No. 45, p. 4720–4725.
A Dopamine Receptor Model and Its Application in the Design of a New Class of Rigid Pyrrolo [2,3–g]isoquinoline Antipsychotics, Gary L. Olson et al. *American Chemical Societe*, (1981) 24/9:1026–1031.
6.2.3 Conformational Restriction, Williams, et al., *Drug Discovery and Development*, The Humana Press, (1987) pp. 54–55.

(List continued on next page.)

*Primary Examiner*—Paul J. Killos
*Attorney, Agent, or Firm*—Gabor L. Szekeres; Robert J. Baran; Martin A. Voet

[57] ABSTRACT

Compounds of the formula

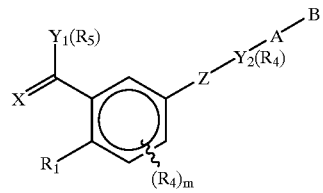

where the symbols have the meaning defined in the specification, have retinoid, retinois antagonist or retinoid inverse agonist type biological activity.

36 Claims, No Drawings

U.S. PATENT DOCUMENTS

| | | | |
|---|---|---|---|
| 5,089,509 | 2/1992 | Chandraratna . | |
| 5,130,335 | 7/1992 | Chandraratna . | |
| 5,134,159 | 7/1992 | Chandraratna . | |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,354,776 | 10/1994 | Chandraratna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Sheh et al. | 560/255 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligond et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,931 | 4/1997 | Beard et al. | 544/224 |
| 5,618,943 | 4/1997 | Vuligonda et al. | 546/342 |
| 5,648,503 | 7/1997 | Vuligonda et al. | 549/13 |
| 5,648,514 | 7/1997 | Johnson et al. | 560/102 |
| 5,654,469 | 8/1997 | Vuligonda et al. | 560/56 |
| 5,663,347 | 9/1997 | Chandraratna | 546/152 |
| 5,663,357 | 9/1997 | Teng et al. | 546/323 |
| 5,663,367 | 9/1997 | Vuligonda et al. | 549/4 |

FOREIGN PATENT DOCUMENTS

| | | | |
|---|---|---|---|
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 85/00806 | 2/1985 | WIPO . | |
| 85/04652 | 10/1985 | WIPO . | |
| 91/16051 | 10/1991 | WIPO . | |
| 92/06948 | 4/1992 | WIPO | C07C 69/86 |
| 93/03713 | 3/1993 | WIPO . | |
| 93/11755 | 6/1993 | WIPO . | |
| 93/21146 | 10/1993 | WIPO | C07C 69/76 |
| 94/14777 | 7/1994 | WIPO . | |
| 95/04036 | 2/1995 | WIPO . | |
| 96/05165 | 2/1996 | WIPO . | |

OTHER PUBLICATIONS

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid and Acitretin on the Proliferation, Lipid Synthesis and Keratin Expression of Cultured Human Sebocytes in Vitro" C.C. Zouboulis, *The Journal of Investigation Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivatives as Potential Anticancer Agents That Inhibit Tubulin Polymerization" by Cushman, Mark et al. *J. Med. Chem.*, (1991), 34:2579–2588.

"Synthesis and Evaluationof New Pretoein Tyrosine Kinase Inhibitors. Part 1. Pyridine–Containing Stilbenes and Amides" by Cushman, Mark et al. *Bioorganic & Medicinal Chemistry Letters*, (1991) 1/4:211–214.

"Di–and Tri–methoxystyryl Derivatives of Heterocyclic Nitrogen Compounds" by Bahner,C. T. et al. *Arzneim–Forsch./Drug Res*, (1981)31 (I), Nr. 3.

"Retinobenzoic acids. 3. Structure–Activity Relationships of Retinoidal Azobenzene–4–Carboxylic Acids and Stilbene–4–Carboxylic Acids" by H. Kagechika et al., *Journal of Medicinal Chemistry*, (1989), 32:1098–1108.

Eyrolles, L. et al. "Retinoid Antagonists: Molecular Design Based on the Ligand Superfamily Concept" *Med. Chem. Res.*, (1992) 2:361–367.

Liu, S. S. et al. "Systemic Pharmacokinetics of Acetylenic Retinoids in Rats", *Drug Metabolism and Disposition*, (1990) 18/6: 1071–1077.

Chemical Abstracts, vol. 122, No. 13, Mar. 27, 1995 abstract no. 151372m, (S. Kaku et al.).

Chemical Abstracts, vol. 117, No. 13 Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 37, No. 10, May 13, 1994, pp. 1508–1517, Laurence Eyrolles.

Journal of Medicinal Chemistry, vol. 39, No. 16, Aug. 2, 1994, pp. 3035–3038, Min Teng et al.

Biochemical and Biophysical Research Communications, vol. 155, No. 1, 1988, pp. 503–508.

Chemical Abstracts. vol. 121, No.9, 1994.

Database WPI, Section Ch, Week 9416, Derwent Publications Ltd. London, GB; Class B05, AN 94–128759 and JP 6078266A, see English language abstract in Derwent.

Journal of Medicinal Chemistry, vol. 38, No. 16, Aug. 4, 1995, pp. 3163–3173.

Weiner, et al., "A phase I trial of topically applied trans–retinoic acid in cervical dysplasia–clinical efficacy", *Investigational New Drugs*, 4:241–244, 1996.

Jones, et al., "A dose–response study of 13–cis–retinoic acid in acne vulgaris", *British Journal of Dermatology*, (1983) 108, 333–343.

Fekrat, et al., "The Effect of Oral 13–cis–retinoic Acid on Retinal Redetachment after Surgical Repair in Eyes with Proliferative Viteoretinopathy", *Ophthalmology*, vol. 102, No. 3 (Mar. 1995), pp. 412–418.

Nagpal, et al., "Separation of Transactivation and AP1 Antagonism Functions of Retinoic Acid Receptor α*", *The Journal of Biological Chemistry*, 270/2(1995): 923–927.

Allegretto, et al., "Transactivation Properties of Retinoic Acid and Retinoid X Receptors in Mammalian Cells and Yeast", *The Journal of Biological Chemistry*, vol. 268, No. 35 (Dec. 15, 1993), pp. 26625–26633.

Gruapner, et al., "6'–Substituted Naphthalene–2–Carboxylic Acid Analogs, A New Class of Retinoic Acid Receptor Subtype–Specific Ligands," *Biochemical and Biophysical Communications*, vol. 179, No. 3 (Sep. 30, 1991), pp. 1554–1561.

Moore, et al., "Retinoic Acid and Interferon in Human Cancer: Mechanistic and Clinical Studies," *Seminars in Hematology*, 31/4, Suppl 5 (Oct. 1994), pp.31–37.

Johnson A. T. et al. "Synthesis and Characterization of a Highly Potent and Effective Antagonist of Retinoic Acid Receptors," Journal of Medicinal Chemistry, vol. 38, No. 24, Nov. 24, 1995, pp. 4764–4767.

Yu K –L et al. "Application of the Heck Reaction in the Synthesis of Truncated Naph–thoic Acid Retinoids" Bioorganic & Medicinal Chemistry Letters, vol. 6, No. 23, 1996.

Arcadi et al. Palladium–Catalyzed Reaction of o–Ethynylphenols, o–((Trimethylsilyl)ethynyl)phenyl Acetates, and o–Alkynylphenols with Unsaturated Triflates or Halides: A Route to 2–Substituted–,2,3–Disubstituted–, and 2–Substituted–3–acylbenzo[bi]furans, 1996, J. Org. Chem 61:9280–9288.

TRISUBSTITUTED PHENYL DERIVATIVES HAVING RETINOID AGONIST, ANTAGONIST OR INVERSE AGONIST TYPE BIOLOGICAL ACTIVITY

BACKGROUND OF THE INVENTION

1. Field of the Invention

The present invention relates to novel compounds having retinoid-like, retinoid antagonist and/or retinoid inverse-agonist-like biological activity. More specifically, the present invention relates to trisubstituted phenyl derivatives which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Several United States Patents assigned to the same assignee as the present application and patents and publications cited therein describe or relate to substituted phenyl derivatives having retinoid like biological activity. Examples of such patents are: U.S. Pat. Nos. 4,980,369; 4,992,468; 5,006,550; 5,013,744; 5,015,658; 5,068,252; 5,130,355; 5,134,159; 5,162,546; 5,202,471; 5,231,113; 5,278,318; 5,324,744; 5,324;840; 5,326,898; 5,346,915; 5,348,975; 5,349,105; 5,391,753; 5,414,007; 5,434,173; 5,498,755; 5,498,795; 5,534,641, and 5,556,996. Still further, several co-pending applications and recently issued patents which are assigned to the assignee of the present application, are directed to further compounds having retinoid-like activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXB_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists.

It has been recently discovered and described in pending applications assigned to the same assignee as the present application that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J Med. Chem. 1995, 38, 3163–3173. Kaneko et al. Med. Chem Res. (1991) 1:220–225; Apfel et al. Proc. Natl. Acad. Sci. USA Vol 89 pp 7129–7133 August 1992 Cell Biology; Eckhardt et al. Toxicology Letters, 70 (1994) 299–308; Keidel et al. Molecular and Cellular Biology, Vol 14, No. 1, January 1994, p 287–298; and Eyrolles et al. J. Med. Chem. 1994, 37, 1508–1517 describe compounds which have antagonist like activity at one or more of the RAR retinoid subtypes.

SUMMARY OF THE INVENTION

The present invention relates to compounds of Formula 1

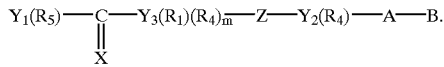

Formula 1 where X is O, S, $C(R_2)$ or $NOR^*$, $R^*$ is H, $C_{1-6}$ alkyl or phenyl;

$R_1$ is H, lower alkyl of 1 to 10 carbons, F, Cl, Br, I, $CF_3$, $OR_2$ $SR_2$, $OCH_2OCl_{1-6}$ alkyl or $CF_2CF_3$;

$R_2$ is independently H, lower alkyl of 1 to 10 carbons, $R_3Si$, or $COR_3$ where $R_3$ is independently H, lower alkyl of 1 to 6 carbons or phenyl;

$R_4$ is lower alkyl of 1 to 6 carbons, F, Cl, Br, I, $CF_3$, $CF_2CF_3$, $NO_2$, $N(R_6)_2$, CN, $COR_3$, or $N(R_6)$—$COR_3$;

m is an integer between 0 and 3;

$Y_1$ is phenyl, naphthyl or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, $COOCl_{1-6}$alkyl; $N_3$; $N(R_6)_2$, OH, $OR_3$; $SR_3$; $OCOR_3$, or $SCOR_3$;

Z is —C≡C—
—N=N—,
—N(O)=N—,
—N=N(O)—,
—N=$CR_6$—,
—$CR_6$=N,
—($CR_6$=$CR_6$)$_n$— where n is an integer having the value 0–5,
—CO—$NR_6$—,
—CS—$NR_6$—,
—$NR_6$—CO,
—$NR_6$—CS,
—COO—,
—OCO—;
—CSO—;
—OCS—;
—CO—$CR_6$=$CR_6$—

$R_6$ is independently H or lower alkyl of 1 to 6 carbons;

$Y_2$ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being unsubstituted or substituted with one or two $R_4$ groups, or when Z is —($CR_6$=$CR_6$)$_n$ and n is 3, 4 or 5 then $Y_2$ represents a direct valence bond between said ($CR_6$=$CR_6$)$_n$ group and B;

$Y_3$ is phenyl, pyridyl, thienyl or furyl unsubstituted or substituted with up to 3 $R_1$ groups and unsubstituted or substituted with up to 3 $R_4$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CH(OR_{13}O)$, —$COR_7$, $CR_7(OR_{12})_2$, $CR_7(OR_{13}O)$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of cancerous and precancerous conditions, including, pre-malignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and decrease in cell proliferation was done by Venna & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in *Cancer Research*: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\Gamma$ receptors, and the ability or inability of the compounds to activate transcription of a reporter gene through these receptor subtypes can be tested.

Specifically, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. *Cell* 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4 \times 10^5$ cells/well) were transiently transfected with the luciferase reporter plasmid MTV-4(R5G)-Luc (0.7 µg/well) containing four copies of the R5G retinoid DNA response element along with the RXRα expression plasmid pRS-hRXRα (0.1 µg/well) and one of the RAR-P-GR expression plasmids (0.05 µg/well) in 12 well plates via calcium phosphate precipitation Chen et al. (1987) Mol. Cell. Biol. 7, 2745–2752, as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS, cells were lysed and luciferase activity was measured as previously described in de Wet et al. (1987) Mol. Cell. Biol. 7, 725–737. Luciferase values represent the mean±SEM of triplicate determinations normalized to β-galactosidase activity.

Table 1 below shows the results of the PGR assay for certain exemplary compounds of the invention for the receptor subtypes in the RAR group and Table 2 shows the results of the ligand binding assay for the same compounds. As it can be seen from the Tables, these exemplary compounds do not transactivate but bind to the receptor and therefore have retinoid antagonist (or inverse agonist) effects.

TABLE 1

PGR Assay Data (transactivation)

| Compound No. | EC$_{50}$ (nanomolar) | | | % Efficiency[1] | | |
|---|---|---|---|---|---|---|
| | RAR$_\alpha$ | RAR$_\beta$ | RAR$_\gamma$ | RAR$_\alpha$ | RAR$_\beta$ | RAR$_\gamma$ |
| 5 | NA[2] | NA | NA | 1 | 3 | 1 |
| 8 | NA | NA | NA | 1 | 3 | 3 |
| 9 | NA | NA | NA | 1 | 3 | 5 |
| 12 | NA | NA | NA | 0 | 1 | 5 |
| 13 | NA | NA | NA | 0 | 0 | 0 |
| 20 | NA | NA | NA | 9 | 5 | 1 |
| 22 | NA | NA | NA | 0 | 0 | 0 |
| 25 | NA | NA | NA | 0 | 2 | 0 |
| 28 | NA | NA | NA | 0 | 0 | 1 |
| 29 | NA | NA | NA | 0 | 0 | 1 |
| 31 | NA | NA | NA | 0 | 4 | 2 |

[1]"% Efficiency" is percentage of efficiency of the test compounds in this essay relative to all-trans-retinoic acid.
[2]"NA" stands for NOT ACTIVE (>10,000 nM)

TABLE 2

Ligand Binding Assay

| Compound No. | Kd (nanomolar) | | |
|---|---|---|---|
| | RAR$_\alpha$ | RAB$_\beta$ | RAR$_\gamma$ |
| 5 | 339 | 98 | 897 |
| 8 | 8205 | 1315 | 5218 |
| 9 | 942 | 152 | 730 |
| 12 | 1447 | 193 | 394 |
| 13 | 1187 | 487 | 902 |
| 20 | >1000 | 224 | >1000 |
| 22 | 1597 | 763 | 1498 |
| 25 | 1154 | 217 | 1960 |
| 28 | 2094 | 538 | 949 |
| 29 | 1160 | 233 | 817 |
| 31 | 3289 | 488 | 366 |

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. *J. Biol. Chem.* 271, 22692–22696 (1996) which is expressly incorporated herein by reference.

In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. *EMBO J.* 12, 2349 –2360 (1993) expressly incorporated herein by reference. Retinoid inverse agonists are able to inhibit the basal luciferase activity in these cells in a dose dependent manner and IC$_{50}$s measured.

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

Generally speaking, compounds of the invention where Z is an ethyne function are obtained in a sequence of reactions which initially involve the synthesis of a halogenated, preferably brominated, phenyl derivative, that has in the position meta to the halogene (preferrably bromo) group an Y(R$_5$)—CO ketone function and which may be obtained as a result of a Friedel-Crafts or like reaction. The bromo compound is reacted with (trimethylsilyl)acetylene to provide a [1-(2-trimethylsilyl)ethynyl]phenyl derivative, from which the trimethylsilyl group is removed by treatment with base. The Y(R$_5$)—CO ketone function may be subjected to a Grignard reaction, followed by dehydration of the resulting tertiary alcohol to provide compounds of the invention where X is CH$_2$. The ethyne compounds are coupled with a reagent of the formula X$_2$—Y$_2$(R$_4$)—A—B where X$_2$ is a halogen and the remaining symbols are defined in connection with Formula 1.

Compounds of the invention where Z is other than the above-described ethyne function, are obtained by utilizing the reactive nature of the bromo group, either to couple the bromo phenyl ketone compound (bromine is in the phenyl group) directly, such as in a Heck reaction, to provide compounds where the Y$_2$(R$_4$)A—B group is attached directly to the phenyl group. Alternatively the bromo function may be converted into other reactive groups, such as NH$_2$, SH, or COOH which is then coupled to a reagent that together with the NH$_2$, SH, or COOH completes the moiety designated Z in Formula 1, and which also introduces the Y$_2$(R$_4$)—A—B moiety of the compounds of the invention. Compounds of the invention where Z represents an ester, amide, thioester, thioamide, or azo linkage can, for example, be prepared in accordance with this general synthetic methodology. During the synthetic manipulation the OH or SH function in the para position of the phenyl ring may be protected by appropriate acid or base labile protecting groups, such as methoxymethyl (MOM), acetyl or trialkylsilyl.

Still further, the Z—Y$_2$(R$_4$)—A—B moiety can be formed in multiple steps starting with the introduction of a two-carbon moiety (such as the CH$_3$CO group) in place of the reactive bromo group of the substituted phenyl nucleus. This type of reaction sequence is suitable, for example, for the preparation of compounds of the invention where Z is —(CR$_6$=CR$_6$)$_n$—, n is 3, 4 or 5 and Y$_2$ represents a direct valence bond between the (CR$_6$=CR$_6$)$_n$ group and B. Details of the above-outlined generalized synthetic schemes are provided below in connection with the description of the specific embodiments and specific examples.

The synthetic methodology employed for the synthesis of the compounds of the present invention may also include transformations of the group designated —A—B in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of q in the compounds of the invention (or precursors thereof) before affecting the coupling or linkage with the phenyl nucleus (where such compounds are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of the invention as set forth in Formula 1 (or precursors thereof) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of the invention or precursors thereof, where the A group has a triple (acetylenic) bond, can be made by reaction of a corresponding aromatic methyl ketone with strong base, such as lithium diisopropylamide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about –10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from the corresponding halogenated aromatic or heteroaromatic compounds, preferably where the halogen is I.

SPECIFIC EMBODIMENTS

With reference to the symbol $Y_1$ in Formula 1, the preferred compounds of the invention are those where $Y_1$ is phenyl, pyridyl, thienyl, furyl and thiazolyl. Among these the phenyl group and particularly methyl substituted phenyl are more preferred. Furthermore, substitution of the $Y_1$ phenyl group with the carbonyl group and the methyl group is preferred in the 1,4 (sara) and 1,3 (meta) positions.

The X group is preferably O (carbonyl function) or $=CH_2$.

The preferred Z (linker) groups are —C≡C—, —CH=CH—, —CONH—, —COO—, —OCO—, —NHCO—, —$(CR_6=CR_6)_n$— and n is 3, or the Z group is absent (n is zero and Y is directly attached to the phenyl ring). Among the foregoing even more preferred are the following: —C≡C—, —C=C—, and —CONH—. Presently —C≡C— is most preferred.

The $Y_2$ group is preferably phenyl, naphthyl, pyridyl, thienyl or furyl. Even more preferred are compounds where $Y_2$ is phenyl. As far as substititutions on the $Y_2$ (phenyl), $Y_2$ (pyridyl) and ($Y_2$) naphthyl groups are concerned, compounds are preferred where the phenyl group is 1,4 (sara) substituted, the naphthyl group is 2,6 substituted and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no or only one optional $R_4$ substituent on the $Y_2$ group, and the preferred $R_4$ substituent is fluoro (F).

$Y_3$ is preferably phenyl. The $Y_3$ phenyl group is preferably substituted in the 1,3 (meta) positions by the $Y_1$ ($R_5$)CX and Z groups. The $R_1$ group is preferably in the 4 (para) position relative ot the Z, and in the 2 (ortho) position relative to the $Y_1$ ($R_5$)CX group.

The A—B group of the preferred compounds is $(CH_2)_q$COOH or $(CH_2)_q$—COOR$_8$, where $R_8$ is defined as above. Even more preferably q is zero and $R_8$ is lower alkyl.

In the preferred compounds of the invention m is 0, that is, there is no $R_4$ substituent on the phenyl ring.

The $R_1$ group of the preferred compounds of the invention is OH, or $OR_2$ where $R_2$ is preferably H, lower alkyl of 1 to 10 carbons, methoxymethyl or dimethyl-t-butylsilyl. Among the $R_2$ alkyl groups methyl and isopropyl are especially preferred.

The most preferred compounds in accordance with Formula 1 are listed below in Table 3 for Formula 2 and with reference to that formula.

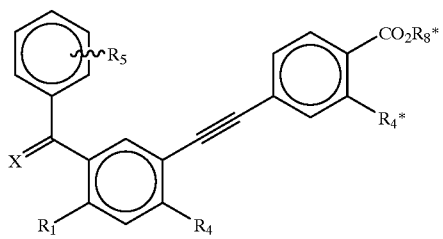

Formula 2

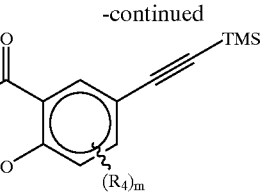

K₂CO₃

Formula 4

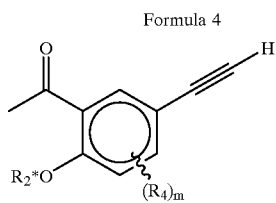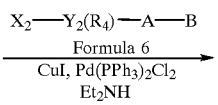

X₂—Y₂(R₄)—A—B
Formula 6
―――――――→
CuI, Pd(PPh₃)₂Cl₂
Et₂NH

Formula 5

TABLE 3

| Compound No. | R₁ | R₄ | X | R₅ | R₄* | R₈* |
|---|---|---|---|---|---|---|
| 3 | OCH₂OCH₃ | H | O | 4-methyl | H | Et |
| 4 | OH | H | O | 4-methyl | H | Et |
| 5 | OH | H | O | 4-methyl | H | H |
| 6 | CH₃COO— | H | CH₂ | 4-methyl | H | Et |
| 7 | OCH₂OCH₃ | H | CH₂ | 4-methyl | H | Et |
| 8 | OH | H | CH₂ | 4-methyl | H | H |
| 9 | OCH₂OCH₃ | H | CH₂ | 4-methyl | H | H |
| 11 | OCH₃ | H | CH₂ | 4-methyl | H | Et |
| 12 | OCH₃ | H | CH₂ | 4-methyl | H | H |
| 13 | OCH₂OCH₃ | H | O | 4-methyl | H | H |
| 15 | O-n-heptyl | H | CH₂ | 4-methyl | H | Et |
| 16 | O-n-heptyl | H | CH₂ | 4-methyl | H | H |
| 19 | H | H | CH₂ | 4-methyl | H | Et |
| 20 | H | H | CH₂ | 4-methyl | H | H |
| 21 | —OCH₃ | H | O | 4-methyl | H | Et |
| 22 | —OCH₃ | H | O | 4-methyl | H | H |
| 23 | OCH₂OCH₃ | CH₃ | O | 4-methyl | F | Et |
| 24 | OH | CH₃ | O | 4-methyl | F | Et |
| 25 | OH | CH₃ | O | 4-methyl | F | H |
| 26 | OCH(CH₃)₂ | H | CH₂ | 4-methyl | H | Et |
| 27 | OCH(CH₃)₂ | H | CH₂ | 4-methyl | F | Et |
| 28 | OCH(CH₃)₂ | H | CH₂ | 4-methyl | H | H |
| 29 | OCH(CH₃)₂ | H | CH₂ | 4-methyl | F | H |
| 30 | OCH(CH₃)₂ | H | CH₂ | 3-methyl | H | Et |
| 31 | OCH(CH₃)₂ | H | CH₂ | 3-methyl | H | H |
| 32 | OSi(CH₃)₂—t-butyl | H | CH₂ | 4-methyl | H | Et |

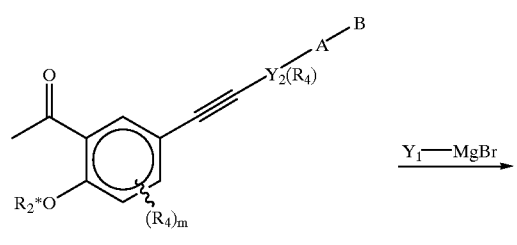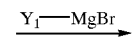

Y₁—MgBr

Formula 7

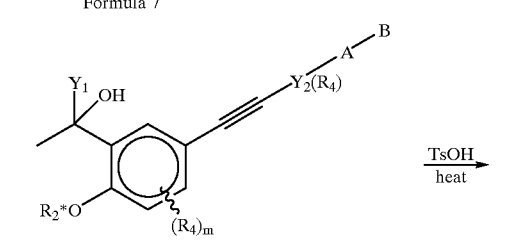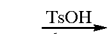

TsOH
―――→
heat

Formula 8

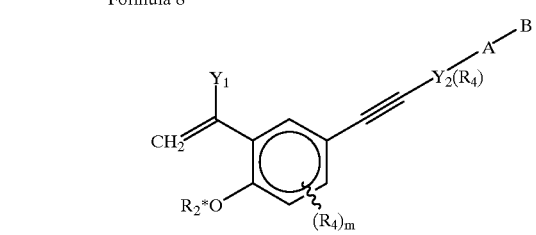

Formula 9

↓

HOMOLOGS and DERIVATIVES

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formula 1.

Reaction Scheme 1

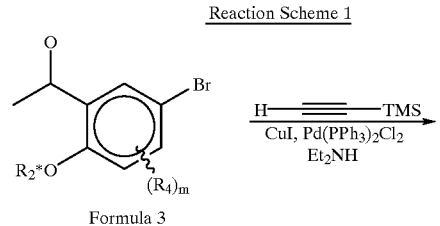

Formula 3

Referring now to Reaction Scheme 1 a synthetic process is disclosed whereby exemplary compounds of the invention are obtained in which, with reference to Formula 1, the Z group is ethynyl (—C≡C—) and the X group is CH₂. The compounds shown in this reaction scheme and in the other reactions schemes of this specification, include an OR₂* substituent where the R₂* group represents the moieties defined as R₂ in connection with Formula 1. However, for the purposes of the reaction schemes the R₂* moiety is distinguished from the R₂ group of the "final" biologically active compounds of the invention, because the synthetic steps involved in the synthesis of the compounds of the invention may require the R₂* to act as protecting group, and not all of the R₂ groups are necessarily suitable for this purpose. Therefore, during the synthetic steps which are only generally described in connection with the reaction schemes, removal and attachments of the various $R_2^*$ groups may become necessary as protection and deprotection of the OH or SH groups. However, these protection and deprotection steps and how to perform them will be readily apparent to those skilled in the art in light of the present disclosure. The synthetic processes disclosed in the reaction schemes of this specification can also be applied for the preparation of compounds where, with reference to Formula 1 the $R_1$ group is other than $OR_2$, or $SR_2$.

The compounds of Formula 3 in Reaction Scheme 1 may be available commercially or can be obtained in synthetic steps which are well known in the chemistry of benzene derivatives. An example for a compound of Formula 3 is 5-bromo-2-methoxyacetophenone, which can be obtained through a Friedel Crafts reaction from 4-bromoanisol, as is described in detail in the Specific Examples. Another example is 5-bromo-2-methoxymethoxyacetophenone which can be obtained from 5-bromo-2-hydroxyacetophenone by treatment with chloromethyl methyl ether in the presence of base. As is shown in Reaction Scheme 1, compounds of Formula 3 are reacted with (trimethylsilyl)acetylene in the presence of copper(I)iodide, diethylamine and bis(triphenylphosphine)palladium(II) chloride to yield the acetophenone derivatives substituted in the meta position with the (trimethylsilyl)ethynyl group (Formula 4). The trimethylsilyl group is removed from the compounds of Formula 4 by treatment with base, such as potassium carbonate, in alcoholic solvent (eg. methanol), to yield the ethynyl substituted acetophenone derivatives of Formula 5. The ethynyl substituted acetophenone derivatives of Formula 5 are then coupled with the reagent of the formula $X_2$—$Y_2(R_4)$—A—B (Formula 6), where $X_2$ is halogen and the remaining symbols are defined in connection with Formula 1. The coupling reaction is conducted in the presence of copper(I)iodide, diethylamine and bis (triphenylphosphine)palladium(II) chloride to provide the disubstituted acetylene compounds of Formula 7. Examples for the reagent $X_2$—$Y_2(R_4)$—A—B (Formula 6) are ethyl 4-iodobenzoate, ethyl 6-bromo-2-naphthoate, ethyl 6-iodonicotinate, ethyl 2-iodofuran-5-carboxylate, and ethyl 2-iodothiophen-5-carboxylate. Precise conditions of the reactions leading from compounds of Formula 3 to the compounds of Formula 7 are described in connection with the specific examples. These reactions are analogous to the reaction described in several United States Letters Patent, such as U.S. Pat. Nos. 5,348,972 and 5,346,915, assigned to the assignee of the present application, where introduction of an ethynyl group into a heteroaryl nucleus and subsequent coupling with a halogenated aryl or heteroaryl function are described. The specifications of U.S. Pat. Nos. 5,348,972 and 5,346,915 are specifically incorporated herein by reference.

The disubstituted acetylene compounds of Formula 7 are then reacted with a Grignard (or similar organometal) reagent having the formula $Y_1$—MgBr, where $Y_1$ is defined as in connection with Formula 1. An example for the $Y_1$—MgBr reagent is the Grignard reagent obtained from para-tolylbromide, other examples are Grignard or organometal reagents obtained from halogenated heteroaryl compounds. The product of the Grignard (or like) reaction is a tertiary alcohol of Formula 8, which is dehydrated by treatment with acid, to provide compounds of Formula 9. The compounds of Formula 9 are within the scope of the invention (X=$CH_2$), and can be converted into further homologs and derivatives in reactions of the type generally described above. A frequently used reaction in this regard is saponification whereby an ester function (represented in Formula 9 by the symbol B) is converted into a carboxylic acid function. Similarly the $R_2^*$ group may represent an acyl function that can be removed by saponification, or $R_2^*$ may represent an acid labile group (such as methoxymethyl) that can be removed to yield compounds of the invention where $R_2$ is H.

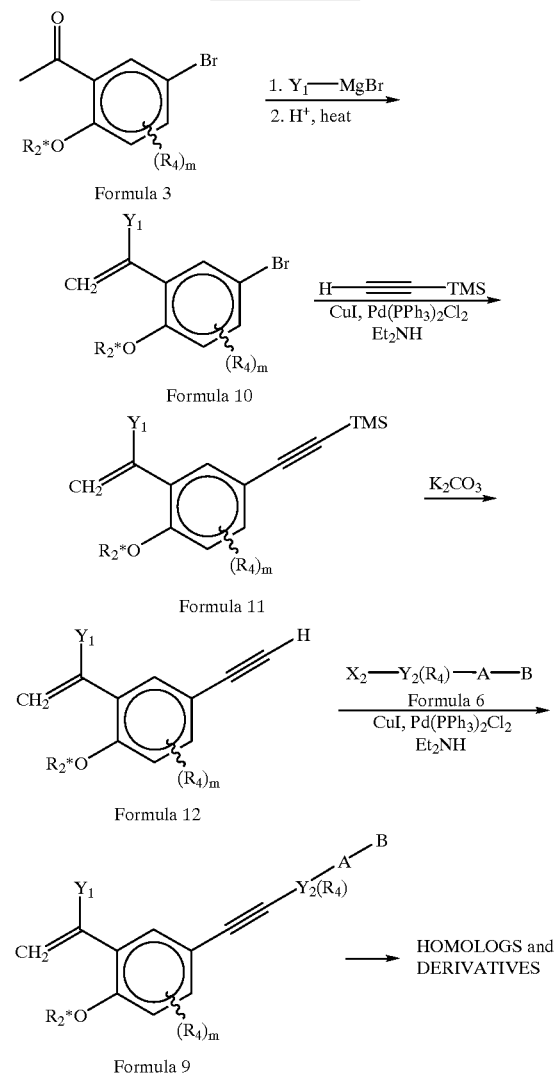

Reaction Scheme 2 discloses another process for synthesizing exemplary compounds of the invention where, with reference to Formula 1, X represents $CH_2$. The reactions in this scheme differ from the reactions illustrated in Scheme 1 primarily in the sequence in which they are conducted. As is shown in Reaction Scheme 2, the brominated acetophenone derivative of Formula 3 is reacted with the Grignard (or similar organometal) reagent having the formula $Y_1$—MgBr, to provide a tertiary alcohol that is dehydrated by treatment with acid, to yield the brominated vinylphenyl compounds of Formula 10. The brominated vinylphenyl compounds of Formula 10 are then coupled with (trimethylsilyl)acetylene, the resulting the (trimethylsilyl) ethynylphenyl compounds (Formula 11) are reacted with base to give ethynylphenyl compounds (Formula 12) which are then coupled with the reagent $X_2$—$Y_2(R_4)$—A—B (Formula 6), in a series of reactions of the type described above in connection with Reaction Scheme 1. The product of the coupling reaction with the reagent X$_2$—Y$_2$(R$_4$)—A—B (Formula 6) is the disubstituted ethynyl derivative of Formula 9 that is within the scope of Formula 1 (X=CH$_2$). The compounds of Formula 9 can be converted to further homologs and derivatives, as described above and indicated in the reaction scheme.

compound of Formula 15; in the preferred example where the reagent is para-toluoyl chloride the compound of Formula 15 is a benzophenone derivative. Thereafter, the ketone compound of Formula 15 is subjected to the sequence of reactions described above, namely coupling with (trimethylsilyl)acetylene, followed by treatment with base, and followed by coupling with the reagent X$_2$—Y$_2$(R$_4$)—A—B (Formula 6), to provide, through the intermediates of

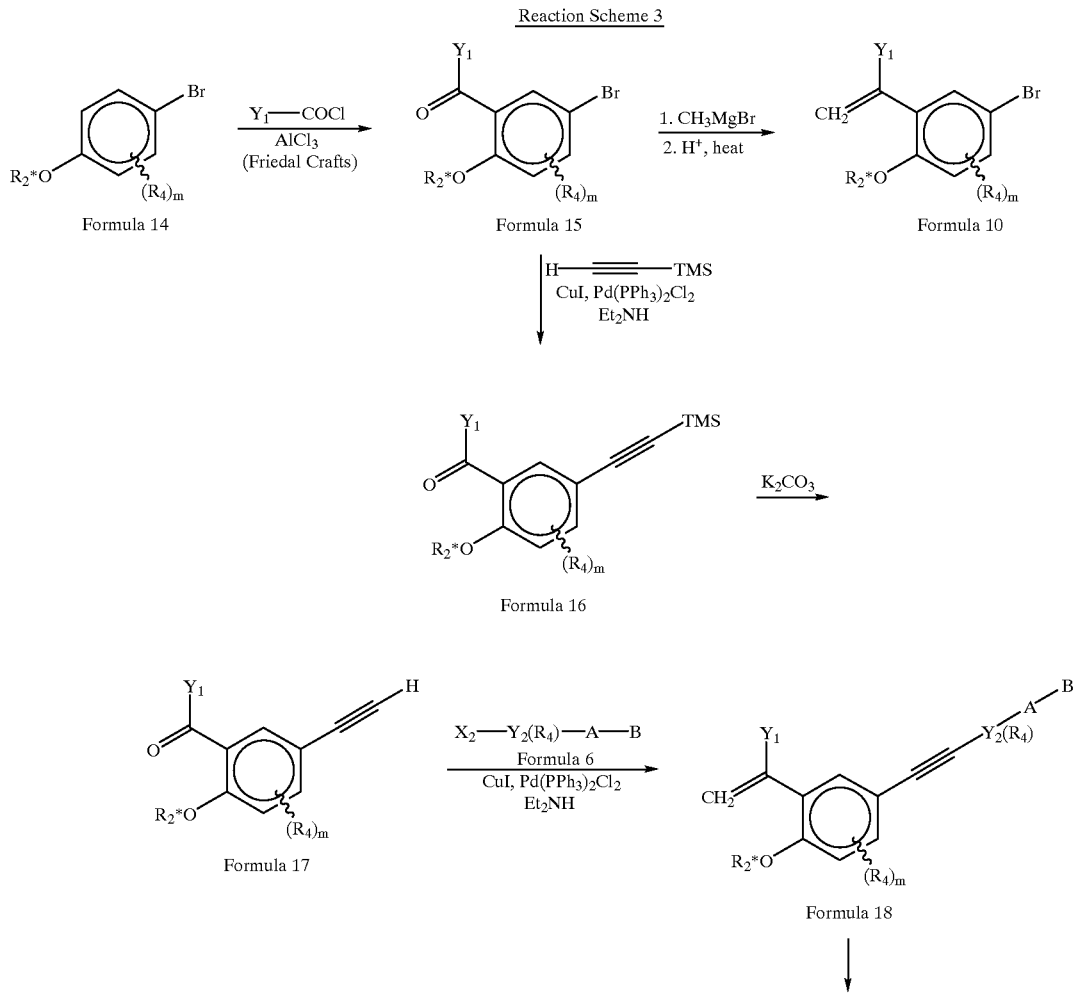

HOMOLOGS and DERIVATIVES

Reaction Scheme 3 discloses a process for synthesis of exemplary compounds of the invention where X of Formula 1 is O. Starting material for this synthesis is a halogen, preferably bromo-substituted phenol derivative of Formula 14 that is protected in the phenolic hydroxyl group. An example is 4-bromoanisole. The compound of Formula 14 is subjected to a Friedel Crafts (or like) reaction with a reagent of the formula Y$_1$—COCl. An example for this reagent, used for the preparation of several preferred compounds of the invention, is para-toluoyl chloride. Other examples are acid chlorides formed from such acids as benzoic acid, nicotinic acid, thiophene-2-carboxylic acid, and furan-2-carboxylic acid. The result of the Friedel Crafts reaction is a ketone Formulas 16 and 17, the ketone compounds within the scope of the invention (Formula 18). The compounds of Formula 18 can be converted into further homologs and derivatives, as described above.

The intermediate brominated benzophenone (or like) derivatives of Formula 15 can also be subjected to a Grignard reaction with methylmagnesium bromide, to provide, after dehydration of the intermediary tertiary alcohol the brominated vinylphenyl compounds of Formula 10. As is described above, the compounds of Formula 10 serve as intermediates in accordance with Reaction Scheme 2 in the synthesis of exemplary compounds of the invention where X of Formula 1 is CH$_2$.

Reaction Scheme 4

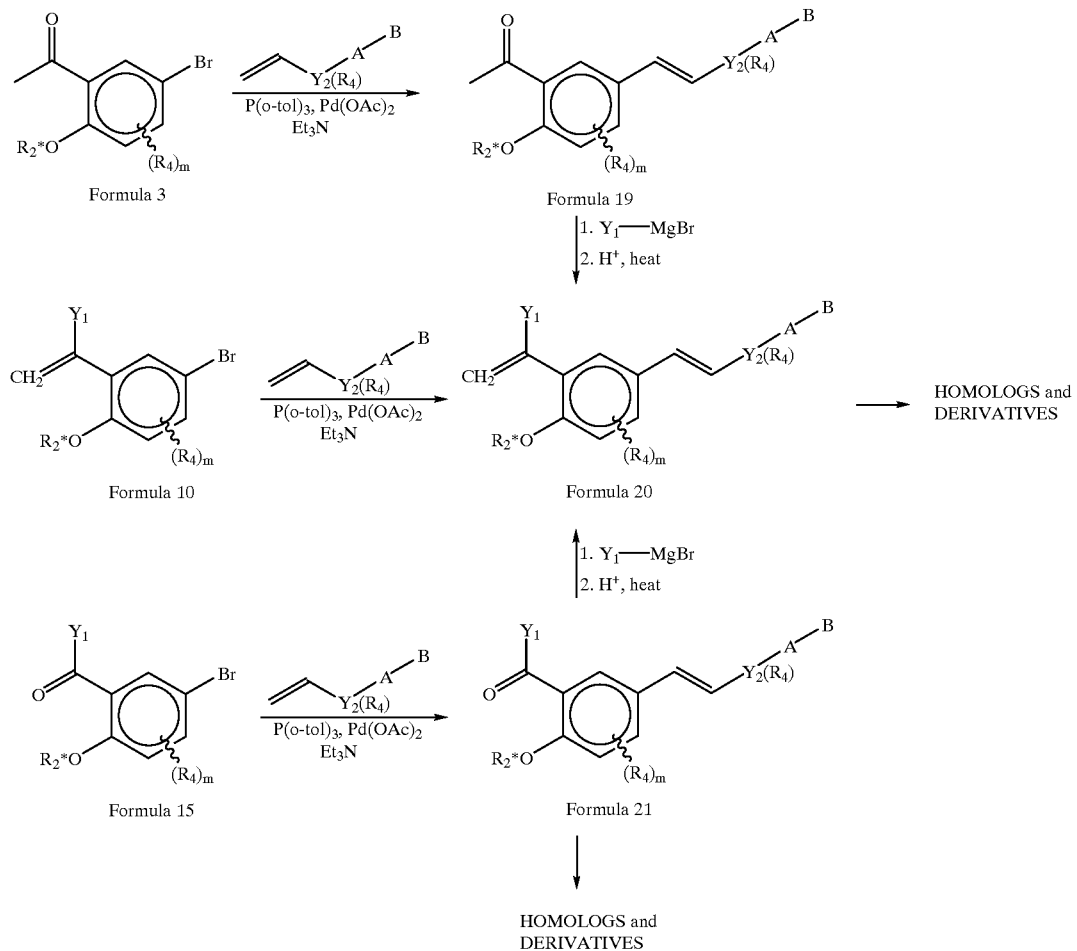

Reaction Scheme 4 discloses synthetic processes for obtaining certain exemplary compounds of the invention in which, with reference to Formula 1, the Z group is —CH=CH—. In accordance with this process brominated acetophenone derivatives of Formula 3 are reacted in a Heck reaction with vinylaryl compounds of the formula $CH_2=CH-Y_2(R_4)-A-B$. Examples for suitable vinylaryl compounds are ethyl 4-vinylbenzoate, ethyl 6-vinyl nicotinate, ethyl 5-vinylfuran-2-carboxylate and ethyl 5-vinylthiophen-2-carboxylate. The Heck reaction is typically conducted in the presence of triethylamine, copper(I) iodide, palladium(II)acetate and tri-(o-tolyl)phosphine. The Heck reaction provides compounds of Formula 19 which are within the scope of the present invention. Depending on the precise nature of the starting compound of Formula 3, its ketone function may need to be protected before the Heck coupling reaction is performed, and the protective group is then removed after the Heck reaction. Suitable protective groups for this purpose are ketal groups, such as the ketal formed under acidic condition with ethyleneglycol. Protection and deprotection of the ketone group of Formula 3 is not shown in the scheme, but will become readily apparent to those skilled in the art in light of the nature of the compound of Formula 3 and the present disclosure. The need for protection and deprotection of the ketone group in the form of a ketal, may also arise in connection with other reactions described in this specification. After the Heck reaction (and deprotection of the ketone function if necessary) the compounds of Formula 19 are reacted in a Grignard (or like organometal) reaction with the reagent $Y_1$—MgBr (or other suitable organometal reagent, $Y_1$—Me where Me is metal such as lithium) to provide after dehydration of the intermediary tertiary alcohol the aryl vinylphenyl compounds of Formula 20 which are within the scope of the invention. The compounds of Formula 20 can be converted to further homologs and derivatives still within the scope of the present invention, as described above.

As is further disclosed in Reaction Scheme 4 the Heck reaction can also be performed on the intermediate brominated arylvinylphenyl compounds of Formula 10, and on the brominated diaryl ketone compounds of Formula 15, which are obtained in accordance with Reaction Schemes 2 and 3, respectively. The products of the Heck reaction of the compounds of Formula 10 with the reagent of the formula $CH_2=CH-Y_2(R_4)-A-B$ are the arylvinylphenyl compounds of the invention of Formula 20. The products of the Heck reaction of the compounds of Formula 15 with the reagent of the formula $CH_2=CH-Y_2(R_4)-A-B$ are the diaryl ketone compounds of the invention of Formula 21, and the latter can be converted into compounds of Formula 20 by reaction with the Grignard reagent $CH_3MgBr$, followed by dehydration of the tertiary alcohol.

The following Reaction Schemes 5, 6, 7 and 8 describe synthetic processes to provide exemplary compounds of the invention starting with the brominated aryl vinylphenyl compounds of Formula 10.

However, those skilled in the art will readily understand that the herein described synthetic steps and processes can be applied with such modifications that are within the skill of the practicing organic chemist, to the brominated acetophenone derivatives of Formula 3 and to the brominated diaryl ketone compounds of Formula 15, and by extension of the herein described generic principles to still further compounds of the invention as well.

Reaction Scheme 5

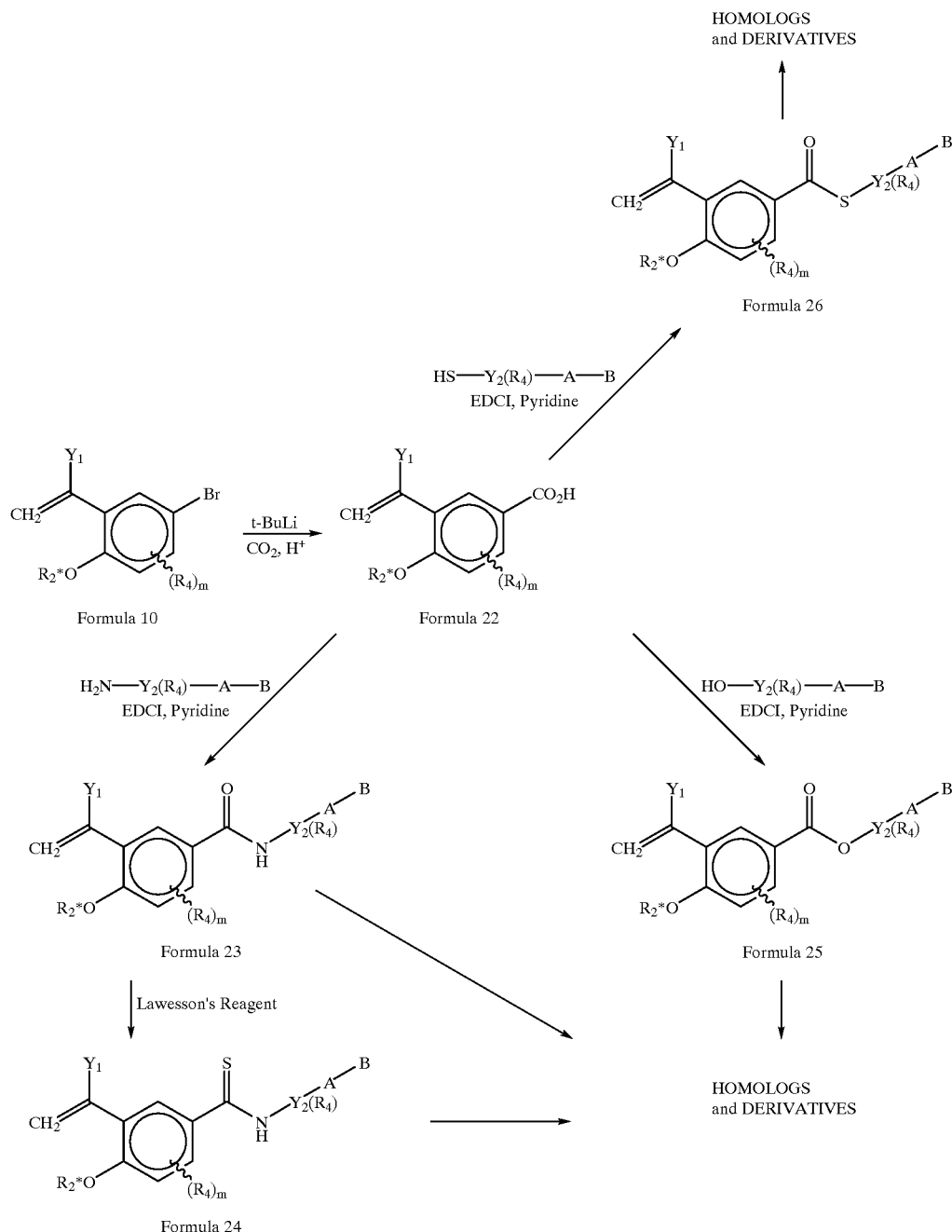

Referring now specifically to Reaction Scheme 5, it discloses synthetic routes to compounds of the invention where, with reference to Formula 1, Z is —CONH— (amides), —COO— (esters) —COS— (thioesters) and —CSNH— (thioamides). In accordance with this scheme the brominated aryl vinylphenyl compounds of Formula 10 are reacted with n-butyl lithium and carbon dioxide to "capture" the carbon dioxide and to provide the aryl vinylbenzoic acid derivatives of Formula 22. The aryl vinylbenzoic acid derivatives of Formula 22 can be converted into amides of Formula 23 by reaction with reagents of the formula $H_2N-Y_2(R_4)-A-B$, into esters of Formula 25 by reaction with reagents of the formula $HO-Y_2(R_4)-A-B$, and into thioesters of Formula 26 by reaction with reagents of the formula $HS-Y_2(R_4)-A-B$, where the symbols are defined as in connection with Formula 1. Examples for the reagents of formula $H_2N-Y_2(R_4)-A-B$ are ethyl 4-aminobenzoate and ethyl 6-aminonicotinate, for the reagents of the formula $HO-Y_2(R_4)-A-B$ ethyl 4-hydroxybenzoate and ethyl 6-hydroxynicotinate, and for the reagents of the formula $HS-Y_2(R_4)-A-B$ ethyl 4-mercaptobenzoate and ethyl 6-mercaptonicotinate. The reactions between the carboxylic acids of Formula 22 and the reagents of the formulas $H_2N-Y_2(R_4)-A-B$, $HO-Y_2(R_4)-A-B$ and $HS-Y_2(R_4)-A-B$, can be performed in several ways in which amides, esters and thioesters are normally prepared. For example, the carboxylic acids of Formula 22 can be activated to form an acid chloride or an activated ester which is thereafter reacted with the amines, alcohols or thioalcohols of the above formulas. More advantageously, however, the formation of the amides, esters or thioesters is performed by condensation of the carboxylic acid of Formula 22 with the amines, alcohols or thiols in a suitable aprotic solvent, such as pyridine, in the presence of a condensing agent such as dicyclohexylcarbodiimide (DCC) or more preferably 1-(3-dimethylaminopropyl)-3-ethylcarbodiimidehydrochloride (EDCl). The amide derivatives of Formula 23 can be readily converted to the thioamides of Formula 24 by reaction with [2,4-bis(4-methoxyphenyl)-1,3-dithia-2,4-diphosphetane-2,4-disulfide] (Lawesson's reagent). The amide derivatives of Formula 23 where the symbol B represents an ester function (such as COOEt) can be readily saponified by treatment with aqueous base, for example LiOH, to yield the corresponding amide derivatives where B represents a free carboxylic acid or its salt. Similar saponification of the esters of Formula 25, or of the thioesters of Formula 26, however is problematic because of the lability of the internal ester and thioester functions. The free acids of these derivatives (where B is COOH or a salt thereof) can be obtained by hydrogenation of the corresponding benzyl esters in which B represents $COOCH_2C_6H_5$.

Reaction Scheme 6

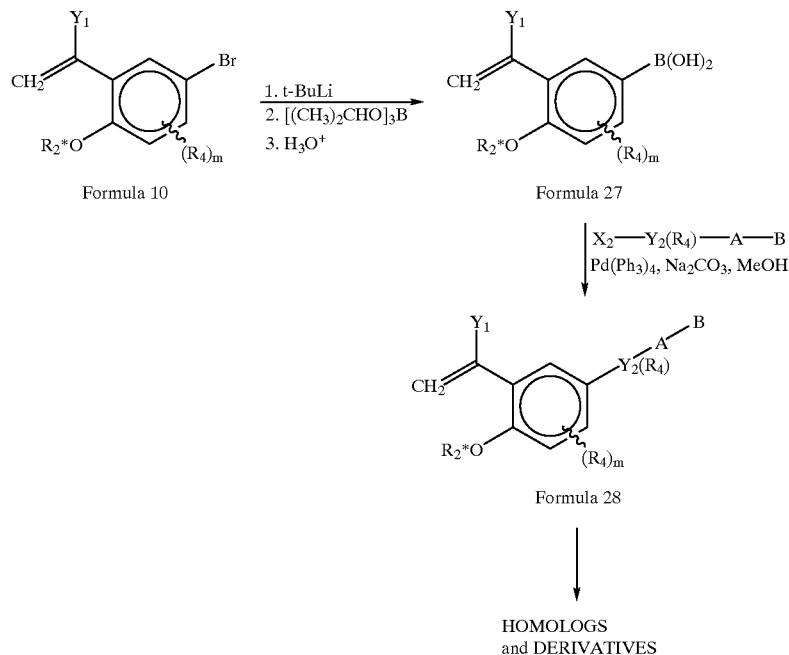

Reaction Scheme 6 discloses a synthetic process for preparing compounds of the invention where, with reference to Formula 1, the Z group is $-(CR_6-C=CR_6)_n-$ and n is 0. In other words, this is a reaction scheme for obtaining compounds of the invention where the $-Y_2(R_4)-A-B$ moiety is directly linked to the position of the phenyl ring which is meta to the $Y_1-C(CH_2)-$ moiety. Pursuant to this reaction scheme, the brominated aryl vinylphenyl compounds of Formula 10 are reacted with t-butyl lithium and subsequently with triisopropylborate to provide the boronic acid derivative intermediates of Formula 27. The boronic acid derivatives of Formula 27 react with compounds of the formula X₂—Y₂(R₄)—A—B (where the symbols are defined as above and X₂ is preferably bromine) in the presence of tetrakis[triphenylphosphine]palladium [Pd (PPh₃)₄] and a base, such as sodium carbonate, to yield compounds of Formula 28. Examples of preferred reagents of formula X₂—Y₂(R₄)—A—B are ethyl 6-bromo-2-naphthoate, ethyl 4-iodobenzoate, ethyl 6-iodonicotinate, ethyl 2-iodofuran-5-carboxylate, and ethyl 2-iodothiophen-5-carboxylate. The compounds of Formula 28 can be converted into further compounds of the invention by the reactions described above, such as saponification, amide formation, homologation and the like.

Reaction Scheme 7

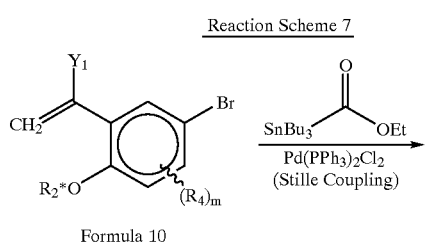

Formula 10

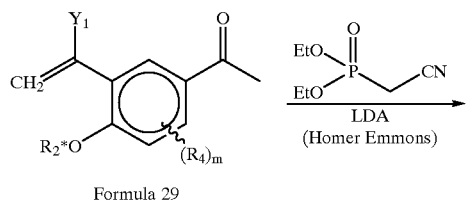

Formula 29

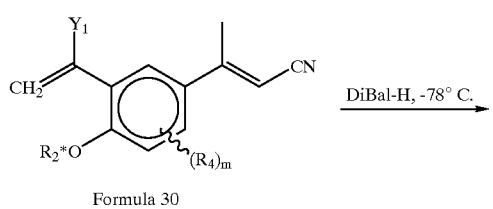

Formula 30

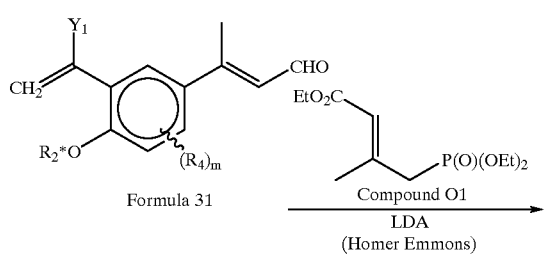

Formula 31

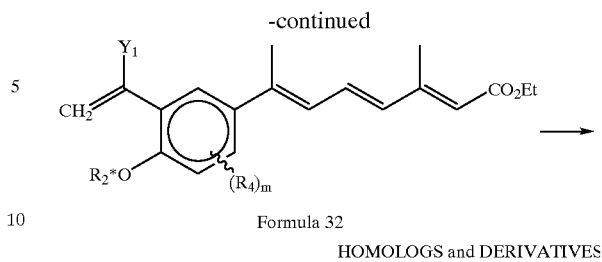

Formula 32

HOMOLOGS and DERIVATIVES

Reaction Scheme 7 discloses a synthetic route for the preparation of compounds where, with reference to Formula 1, Z is —(CR₆=CR₆)ₙ—, n is 3 and the B group is directly attached to the Z group. Thus, in accordance with this scheme the brominated aryl vinylphenyl compounds of Formula 10 are reacted with (1-ethoxyvinyl)tributyltin in the presence of bis(triphenylphosphine)palladium(II) chloride to introduce the acetyl group into the position of the phenyl ring which is meta to the Y₁—C(CH₂)— moiety, and yield the acetophenone derivatives of Formula 29. The latter reaction is known in the art as a Stille coupling. The acetophenone derivatives of Formula 29 are then reacted in a Horner Emmons reaction, in the presence of strong base such as lithium diisopropylamide (LDA), with diethylcyanomethyl phosphonate. The latter reagent is commercially available. The product of the Horner Emmons reaction is an arylvinylphenyl compound of Formula 30 that is substituted in the meta position with a 1-methyl-2-cyanoethenyl group. Those skilled in the art will readily understand that instead of a Horner Emmons reaction the compounds of Formula 30 can also be obtained as a result of an analogous Wittig reaction.

Referring still to Reaction Scheme 7, the cyano function of the compounds of Formula 30 is reduced with a mild reducing agent, such as diisobutylaluminum hydride (Dibal-H) to provide the aldehyde compounds of Formula 31. Another Horner Emmons reaction performed on the aldehydes of Formula 31 with the reagent diethyl(E)-3-ethoxycarbonyl-2-methylallylphosphonate (Compound O1) provides compounds of Formula 32 which are within the scope of the present invention. Compound O1 can be prepared from commercially available ethyl (2)-3-formyl-2-butenoate according to the literature of Corey et al. *J. Org. Chem.* 1974, 39, 921. It will be readily apparent to those skilled in the art that the herein described exemplary synthetic process can be readily adapted or modified by utilizing analogous phosphonate or phosponium salt reagents in Horner Emmons or Wittig reactions, respectively, to obtain additional compounds within the scope of Formula 1 in which Z is —(CR₆=CR₆)ₙ—, and n is 3–5. The compounds of Formula 32 can be converted into further compounds within the scope of the invention by reactions such as saponification, amide formation, reduction to the aldehyde or alcohol stage, and the like. This is indicated in the reaction scheme by conversion to "homologs and derivatives".

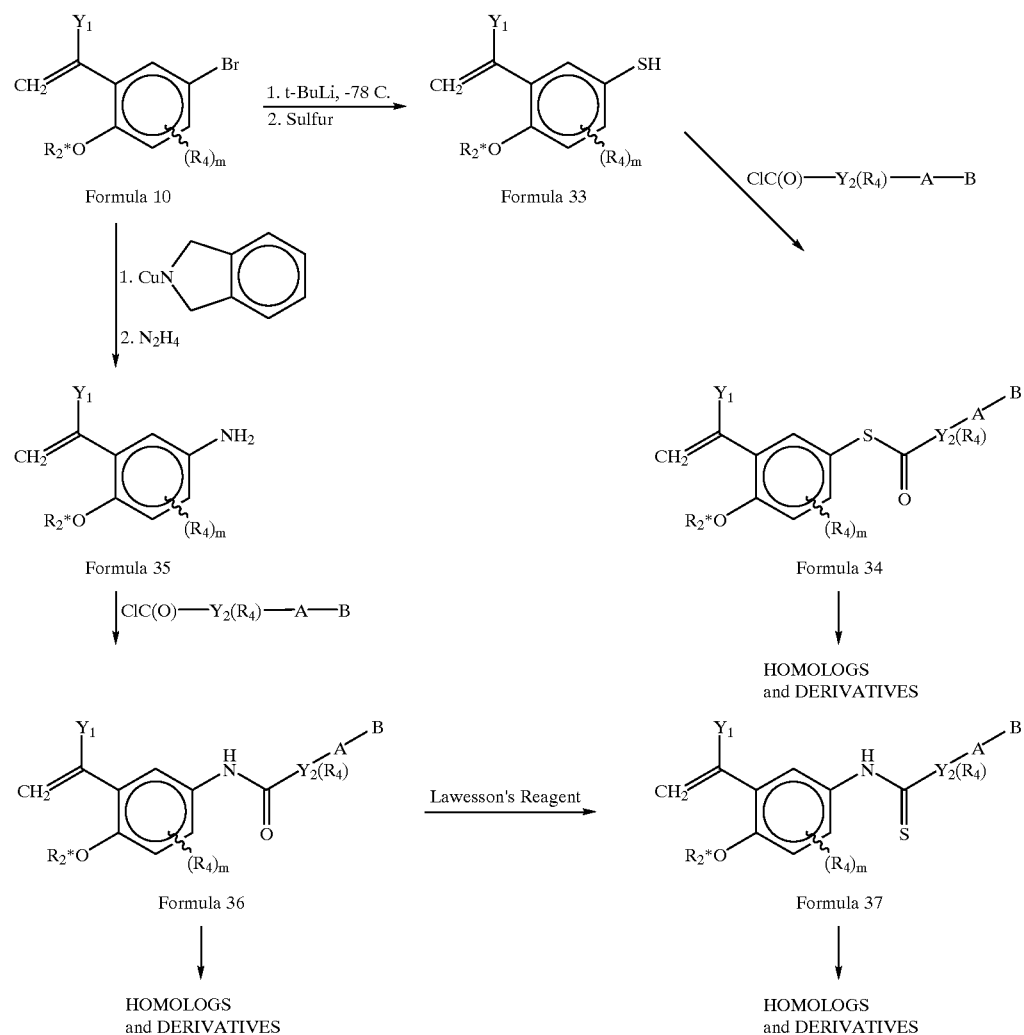
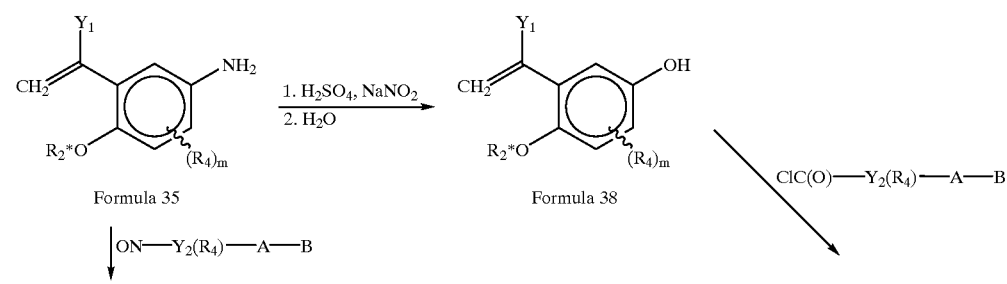

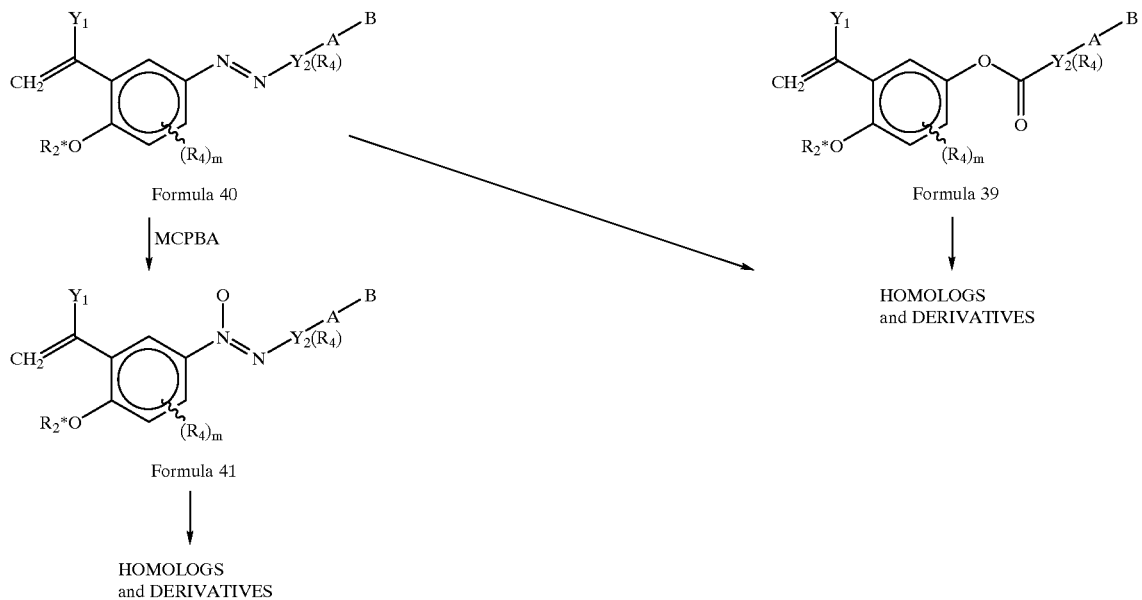

Formula 40 → (MCPBA) → Formula 41 → HOMOLOGS and DERIVATIVES

Formula 39 → HOMOLOGS and DERIVATIVES

Synthetic routes for the preparation of compounds of Formula 1 where the Z is —SCO— (thioester), —NHCO— (amide) —NHCS— (thioamide) —OCO— (ester) of the order "reverse" to the one described in connection with Reaction Scheme 5, as well as where Z is —N=N— (azo) and —N=N(=O)— (azoxide) are disclosed in Reaction Schemes 8 and 9. As is first shown in Reaction Scheme 8 the brominated aryl vinylphenyl compounds of Formula 10 are reacted with t-butyl lithium, and thereafter with sulfur to provide the (arylvinyl)thiophenol compounds of Formula 33. The thiophenol compounds of Formula 33 are reacted with a carboxylic acid, or an activated form of the carboxylic acid, which forms a thioester and introduces the —CO—$Y_2(R_4)$—A—B moiety into the molecules. Those skilled in the art will understand that just as it is described in connection with the amide, ester and thioester formations in Reaction Scheme 5, various activated forms of carboxylic acids are suitable for this purpose. The instant reaction scheme illustrates the method of using acid chlorides of the formula ClCO—$Y_2(R_4)$—A—B in these reactions. Examples for the acid chlorides of formula ClCO—$Y_2(R_4)$—A—B are $ClCOC_6H_4COOEt$ $ClCOC_6H_4COOCH_2C_6H_5$ (the monochlorides of terephthalic acid ethyl and benzyl esters), and $ClCOC_5NH_3COOEt$ and $ClCOC_5NH_3COOCH_2C_6H_5$ (the monochlorides of pyridine 3,6,-dicarboxylic acid ethyl and benzyl esters). The thioesters of Formula 34 are within the scope of the present invention. In order to obtain compounds within the scope of Formula 34 where the B group is a free carboxylic acid (or salt thereof), the thioester is prepared first where the B group is —$COOCH_2C_6H_5$. The benzyl group is then removed by hydrogenation to provide the free acid.

As is shown further in Reaction Scheme 8, the brominated aryl vinylphenyl compounds of Formula 10 are reacted with the cuprous salt of phthalimide and therafter with hydrazine to provide the (arylvinyl)aniline derivatives of Formula 35. These are reacted with the acid chlorides of formula ClCO—$Y_2(R_4)$—A—B to yield the amides of Formula 36 which are within the scope of the invention. The amides of Formula 36 are converted into thioamides of Formula 37 by treatment with [2,4-bis(4-methoxyphenyl)-1,3-dithia-2,4-diphosphetane-2,4-disulfide] (Lawesson's reagent). The amides and thioamides of Formula 36 and 37 can be subjected to transformations (including saponification of an ester group when B is $COOR_8$) to yield further compounds within the scope of the present invention.

Referring now to Reaction Scheme 9, the (arylvinyl) aniline derivatives of Formula 35 are converted to diazonium salt and thereafter to (arylvinyl)phenol derivatives of Formula 38. The (arylvinyl)phenol derivatives of Formula 38 are then converted into esters of Formula 39 by reaction with the acid chlorides of the formula ClCO—$Y_2(R_4)$—A—B or with other activated forms of the carboxylic acids of the general formula HOCO—$Y_2(R_4)$—A—B. As it is described in connection with Reaction Scheme 5, the ester formation may be affected with the free carboxylic acid in an aprotic solvent, such as pyridine, in the presence of dicyclohexylcarbodiimide (DCC) or more preferably 1-(3-dimethylaminopropyl)-3-ethylcarbodiimidehydrochloride (EDCl). In order to obtain free carboxylic acids within the scope of Formula 39 (compounds where B is COOH or a salt therof) the benzyl ester (B=$COOCH_2C_6H_5$) is prepared first, and the benzyl protecting group is thereafter removed by hydrogenation.

In order to obtain compounds of Formula 1 where the Z group is —N=N— (azo) or —N(O)=N— (azoxy) the (arylvinyl)aniline derivatives of Formula 35 are reacted with nitroso compounds of the formula ON—$Y_2(R_4)$—A—B. Examples for reagents of formula ON—$Y_2(R_4)$—A—B are ethyl 4-nitrosobenzoate, ethyl 6-nitroso-2-naphthoate, ethyl 4-nitrosobenzoate, ethyl 6-nitroso-nicotinate, ethyl 2-nitroso-furan-5-carboxylate, and ethyl 2-nitroso-thiophen-5-carboxylate. The azo compounds of Formula 40 can be converted to the azoxy compounds of Formula 41 by oxidation with oxidizing agents known in the art, for example with meta-chloroperoxybenzoic acid (MCPBA).

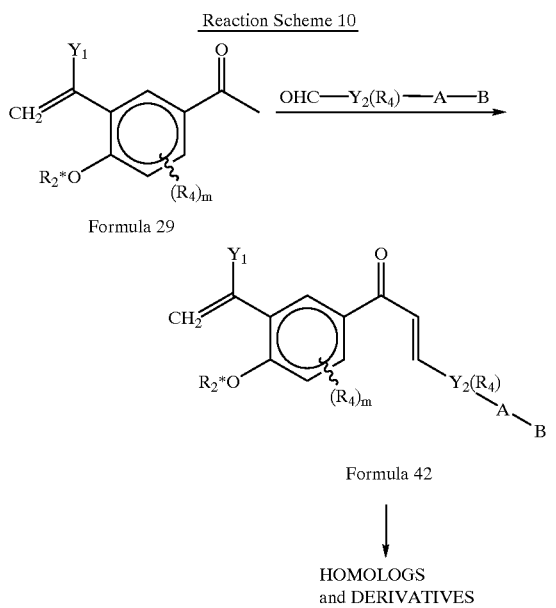

Reaction Scheme 10

Formula 29

Formula 42

↓

HOMOLOGS
and DERIVATIVES

Reaction Scheme 10 discloses a synthetic route for the preparation of exemplary compounds where, with reference to Formula 1, Z is —CO—CR$_6$═CR$_6$—, that is the preparation of compounds which are α-unsaturated ketone derivatives (chalcones). In accordance with this scheme the acetophenone derivatives of Formula 29 (obtained by Stille coupling as shown in Reaction Scheme 7) are reacted in a condensation reaction with a reagent of the formula OHC—Y$_2$(R$_4$)—A—B to yield compounds of Formula 42 which are within the scope of the invention. An example for the reagent OHC—Y$_2$(R$_4$)—A—B is 4-carboxybenzaldehyde that is available commercially. Examples of other reagents suitable for the condensation reaction and for the synthesis of compounds of Formula 42 are:

5-carboxy-pyridine-2-aldehyde, 4-carboxy-pyridine-2-aldehyde,
4-carboxy-thiophene-2-aldehyde, 5-carboxy-thiophene-2-aldehyde,
4-carboxy-furan-2-aldehyde, 5-carboxy-furan-2-aldehyde,
4-carboxyacetophenone, 2-acetyl-pyridine-5-carboxylic acid,
2-acetyl-pyridine-4-carboxylic acid, 2-acetyl-thiophene-4-carboxylic acid,
2-acetyl-thiophene-5-carboxylic acid, 2-acetyl-furan-4-carboxylic acid, and
2-acetyl-furan-5-carboxylic acid. The latter compounds are available in accordance with the chemical literature; see for example Decroix et al J. *Chem Res.* (S), 1978, 4, 134; Dawson et al. *J. Med. Chem.*, 1983, 29, 1282; and Queguiner et al., *Bull. Spc. Chimique de France*, 1969, No. 10, pp 3678–3683. The condensation reaction between the compounds of Formula 29 and the aldehyde of the formula OHC—Y$_2$(R$_4$)—A—B (or an analoguous ketone compound) is conducted in the presence of base in an alcoholic solvent. Preferably, the reaction is conducted in ethanol in the presence of sodium hydroxide. Those skilled in the art will recognize this condensation reaction as an aldol condensation, and in case of the herein described preferred examples (condensing a ketone of Formula 29 with an aldehyde) as a Claisen-Schmidt reaction. (See March: Advanced Organic Chemistry: Reactions, Mechanisms, and Structure, pp 694 695 McGraw Hill (1968). The compounds of Formula 42 are within the scope of the present invention, and can also be subjected to further transformations resulting in additional compounds of the invention designated in the scheme as "homologs and derivatives".

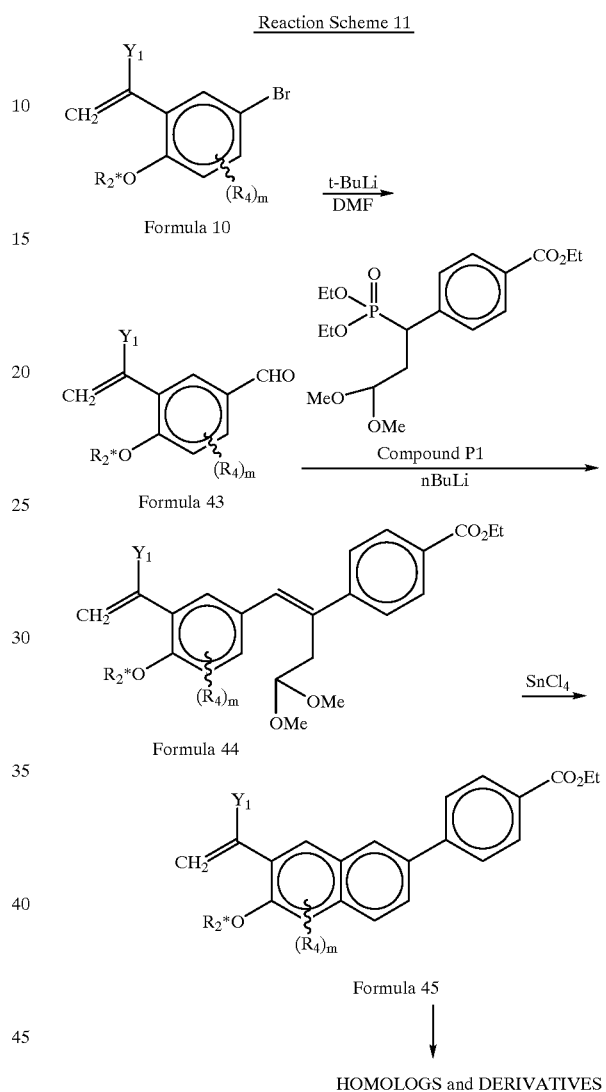

Reaction Scheme 11

Formula 10

Formula 43

Formula 44

Formula 45

↓

HOMOLOGS and DERIVATIVES

Reaction Scheme 11 provides an example for synthesis of compounds of the invention where the Y$_3$ group is naphthyl substituted in the 1,7 positions by the Y$_1$(R$_5$)CX and Z groups, and where Z is —(CR$_6$═CR$_6$)$_n$—, and n is 0. More specifically, Reaction Scheme 11 provides an example for synthesis of compounds of the invention where the Y$_3$ naphthyl group is directly attached to the Y$_2$—A—B group. In accordance with this reaction scheme, the bromo compounds of Formula 10 are reacted with dimethylformamide in the presence of t-butyl lithium to yield the benazaldehyde derivatives of Formula 43. The benzaledehyde derivatives of Formula 43 are subjected to a Horner Emmons type reaction, in the presence of strong base such as n-butyl lithium in hexane, with a 1-aryl or 1-heteroaryl 1-diethoxyphosphoryl-3,3-dimethoxypropane derivative, such as ethyl 4-(diethoxyphosphoryl-3,3-dimethoxypropyl)benzoate (Compound P1). Ethyl 4-(diethoxyphosphoryl-3,3-dimethoxypropyl)benzoate (Compound P1) is available in accordance with the procedure of EPO Application No. 0

210 929 (published on Feb. 4, 1987, Shroot et al.) which is incorporated herein by reference. In accordance with the Shroot et al. reference the reagent ethyl 4-(diethoxyphosphoryl-3,3-dimethoxypropyl)benzoate is made starting with ethyl 4-bromobenzoate that is reacted with dimetyl acetal of acryl aldehyde, the product is hydrogenated and subsequently brominated (with N-bromo succinimide) and thereafter reacted with triethylphosphite. Examples for phoshonates analogous to Compound P1 in that they are suitable for a Horner Emmons reaction with the benzaldehyde derivatives of Formula 43 are ethyl 2-(diethoxyphosphoryl-3,3-dimethoxypropyl)pyridine-5-carboxylate, ethyl 2-(diethoxyphosphoryl-3,3-dimethoxypropyl)pyridine-6-carboxylate, ethyl 2-(diethoxyphosphoryl- 3,3-dimethoxypropyl)thiophene-4-carboxylate, ethyl 2-(diethoxyphosphoryl-3,3-dimethoxypropyl)thiophene-5-carboxylate, ethyl 2-(diethoxyphosphoryl-3,3-dimethoxypropyl)furan-4-carboxylate, ethyl 2-(diethoxyphosphoryl-3,3-dimethoxypropyl)furan-5-carboxylate. These and analogous phosphonate reagents can be obtained by appropriate modification of the procedure described in the Shroot et al. reference.

The product of the Horner Emmons reaction between the benzaldehyde derivatives of Formula 43 and ethyl 4-(diethoxyphosphoryl-3,3-dimethoxypropyl)benzoate (Compound P1) is a disubstituted ethene compound of Formula 44. Those skilled in the art will readily understand that instead of a Horner Emmons reaction, a Wittig reaction can also be employed, utilizing the appropriate phosphonium derivative, to provide compounds of Formula 44. The disubstituted ethene compounds of Formula 44 are cyclized, for example by heating in a neutral solvent (such as dischloromethane), in the presence of $SnCl_4$ or other suitable Friedel Crafts type catalyst, to form the "B ring" of the naphthalene derivatives of the invention, as shown in Formula 45. The compounds of Formula 45 can be converted into further compounds of the invention by reaction well known to the synthetic organic chemist, such as saponification, esterification, amide formation and homologation. This is indicated in Reaction Scheme 11 as conversion to "homologs and derivatives".

SPECIFIC EXAMPLES

Ethyl 4-iodobenzoate (Compound A)

To a suspension of 24.9 g (100.4 mmol) of 4-iodobenzoic acid in 46.25 g (58.9 mL, 1.0 mol) of ethanol was added 3 mL of c. sulfuric acid. The resulting mixture was refluxed for 60 minutes, distilled until a clear, homogeneous solution was obtained and then allowed to cool to room temperature. The reaction mixture was extracted and partitioned between pentane (250 mL) and water (250 mL) and the layers were separated. The aqueous phase was washed with 3×100 mL-portions of pentane. All organic phases were combined, washed with brine, dried over $MgSO_4$, filtered and concentrated in vacuo to a dark yellow oil. Purification by flash chromatography (silica, 10% ethyl acetate in hexane) yielded the title compound as a clear, light yellow oil.

PMR ($CDCl_3$): δ 1.39 (3H, t, J=7.2 Hz), 4.37 (2H, q, J=7.2 Hz), 7.73–7.82 (4H, m).

2-Fluoro-4-iodobenzoic acid (Compound B)

A round bottom (RB) flask containing a solution of 8.0 g (27.0 mmol) of sodium dichromate in 44 mL of glacial acetic acid was placed in an external water bath (21° C.) and left exposed to air. To the resultant orange slurry was added 3.2 g (13.6 mmol) of 2-fluoro-4-iodotoluene followed by the dropwise addition of 22 mL of c. sulfuric acid via syringe (caution: if added too quickly there is a tendency for the mixture to erupt). After the addition of approximately 8 mL of sulfuric acid, a green solid precipitated and the water bath temperature had risen (25° C.). The green reaction mixture was heated in an oil bath (90° C.) for one hour, allowed to cool to ambient temperature, diluted with 1N NaOH solution (aq.) and ethyl acetate (500 mL) and then quenched with sat. $NaHCO_3$ (aq.) solution. The organic phase was separated and washed with water and brine, dried over $MgSO_4$, filtered and concentrated in vacuo to an orange oil. Residual acetic acid was removed by further extraction between ethyl acetate and sat. $NaHCO_3$ (aq.) solution and washing of the organic phase with water and brine. The organic phase was dried over $MgSO_4$, filtered and concentrated in vacuo to give the title compound as an orange solid.

PMR (DMSO-$d_6$): δ 7.61 (1H, t, J=8.0 Hz, J (C-F)=8.0 Hz), 7.67 (1H, dd, J=1.5, 8.2 Hz), 7.78 (1H, dd, J=1.5 Hz, J (C-F)=8.9 Hz).

Ethyl 2-fluoro-4-iodobenzoate (Compound C)

To a solution of 2.5 g (27.0 mmol) of 2-fluoro-4-iodobenzoic acid (Compound B) in 11 mL (8.6 g, 187.5 mmol) of ethanol was added 0.3 mL of c. sulfuric acid. The reaction mixture was heated to reflux in an oil bath (90° C.) for 1.75 hours, fitted with a short path distillation apparatus, distilled and then allowed to cool to ambient temperature. The reaction mixture was extracted and partitioned between pentane and water and the layers were separated. The aqueous phase was washed with pentane and the organic phases were combined. The combined organic phase was washed sequentially with sat. $NaHCO_3$ (aq.) solution, water and brine, dried over $MgSO_4$, filtered and concentrated in vacuo to a purple oil. Purification by flash chromatography (silica, 10% ethyl acetate in hexane) gave the title compound as an orange oil.

PMR ($CDCl_3$): δ 1.39 (3H, t, J=7.1 Hz), 4.39 (2H, q, J=7.1 Hz), 7.52–7.67 (3H, m).

4-bromophenyl acetate (Compound D)

To a solution of 10.0 g (57.8 mmol) of 4-bromophenol in 100 mL of acetonitrile was added 9.6 g (69.5 mmol) of potassium carbonate. A white slurry was obtained to which was added 8.6 mL (121.0 mmol) of acetyl chloride and the resultant reaction mixture was stirred at ambient temperature for 17.5 hours. The reaction mixture was filtered, washed with ethyl acetate and the filtrate was concentrated in vacuo to a yellow oil. Purification by flash chromatography (silica, 10% ethyl acetate in hexane) gave the title compound as a clear, nearly colorless oil.

PMR ($CDCl_3$): δ 2.30 (3H, s), 6.98 (2H, d, J=8.9 Hz), 7.49 (2H, d, J=8.9 Hz).

4-Bromo-1-methoxy-3-methylbenzene (Compound E)

To a solution of 0.8 g (4.4 mmol) of 4-bromo-3-methylphenol in 20 mL of acetone was added 1.5 g (10.9 mmol) of potassium carbonate. A yellow slurry was obtained to which was added 0.55 mL (1.25 g, 8.8 mmol) of methyl iodide. The resultant reaction mixture was stirred at ambient temperature for 12.25 hours, filtered and extracted between ethyl ether and water. The layers were separated and the organic phase was washed with sat. $Na_2SO_3$ (aq.) solution, dried over MgSO$_4$, filtered and then concentrated in vacuo to a yellow oil. Purification by flash chromatography (silica, 10% ethyl acetate in hexane) gave the title compound as a yellow oil.

PMR (CDCl$_3$): δ 2.36 (3H, s), 6.63 (1H, dd, J=3, 8.8 Hz), 6.79 (H, d, J=3 Hz), 7.40 (1H, d, J=8.8 Hz).

5-Bromo-2-hydroxyacetophenone (Compound F)

Under a blanket of argon, an amalgam of 10.0 g (46.4 mmol) of 4-bromophenyl acetate (Compound D) and 6.9 g (51.8 mmol) of aluminum chloride was heated in an oil bath (130° C.) for 30 minutes to give a yellow slurry. The slurry was cooled to 0° C. in an ice bath, diluted with 200 mL of crushed ice and extracted with dichloromethane (twice). The organic phases were combined and then washed with water and brine, dried over MgSO$_4$, filtered and concentrated in vacuo to give a yellow-green solid. Purification by flash chromatography (silica, 5% ethyl acetate in hexane) gave the title compound as a white solid.

PMR (CDCl$_3$): δ 2.63 (3H, s), 6.90 (1H, d, J=8.9 Hz), 7.54 (1H, dd, J=2.5, 8.9 Hz), 7.84 (1H, d, J=2.5 Hz), 12.17 (1H, s).

5-Bromo-2-methoxyacetophenone (Compound G)

To a slurry of 8.55 g (64.2 mmol) of aluminum chloride in 75 mL of dichloromethane cooled to 0° C. (under a blanket of argon) was added dropwise a solution of 10.0 g (53.5 mmol) of 4-bromoanisole and 4.6 mL (64.2 mmol) of acetyl chloride in 25 mL of dichloromethane. After the addition was complete, the clear yellow solution was stirred at 0° C. for 15 minutes, poured into 200 mL of 10% HCl (aq.) solution, cooled to 0° C. in an ice bath and then extracted with dichloromethane (3×200-mL portions). The organic phases were combined and then washed with water and brine, dried over MgSO$_4$, filtered and concentrated in vacuo to give a yellow semi-solid. Purification by flash chromatography (silica, 10% ethyl acetate in hexane) gave the title compound as a white solid.

PMR (CDCl$_3$): δ 2.60 (3H, s), 3.91 (3H, s), 6.86 (1H, d, J=8.9 Hz), 7.55 (1H, dd, J=2.7, 8.9 Hz), 7.84 (1H, d, J=2.7 Hz).

5-Bromo-2-methoxy-4'-methylbenzophenone (Compound H)

Employing the same general procedure as for the preparation of 5-bromo-2-methoxyacetophenone (Compound G), 1.3 mL (1.7 g, 9.2 mmol) of 4-bromoanisole was converted into the title compound using 1.5 g (11.3 mmol) of aluminum chloride, 1.3 mL (1.6 g, 10.1 mmol) of p-toluoyl chloride and 20 mL of dichloromethane. Deviations from the general procedure involved continued overnight stirring (ambient temperature, 16.75 hours) following stirring at 0° C. for 35 minutes and using a 10% solution of c. H$_2$SO$_4$ in crushed ice (v/v) instead of cold 10% HCl (aq.) solution during the subsequent workup procedure. Purification by flash chromatography (silica, 10% ethyl acetate in hexane) gave the title compound as a white solid.

PMR (CDCl$_3$): δ 2.42 (3H, s), 3.72 (3H, s), 6.87 (1H, d, J=8.9 Hz), 7.24 (2H, d, J=8 Hz), 7.43 (1H, d, J=2.6 Hz), 7.54 (1H, dd, J=2.6, 8.9 Hz), 7.70 (2H, d, J=8 Hz).

5-Bromo-2-methoxy-4-methyl-4'-methylbenzophenone (Compound I)

Employing the same general procedure as for the preparation 5-bromo-2-methoxy-4'-methylbenzophenone (Compound H), 780 mg (3.9 mmol) of 4-bromo-1-methoxy-3-methylbenzene (Compound E) was converted into the title compound using 260 mg (1.9 mmol) of aluminum chloride, 0.6 mL (0.7 g, 4.7 mmol) of p-toluoyl chloride and 17 mL of dichloromethane. Purification by flash chromatography (silica, 5% ethyl acetate in hexane) gave the title compound as a white solid.

PMR (CDCl$_3$): δ 2.40 (3H, s), 2.44 (3H, s), 3.69 (3H, s), 6.86 (1H, s), 7.22 (2H, d, J=8.2 Hz), 7.48 (1H, s), 7.69 (2H, d, J=8.2 Hz).

5-Bromo-2-methoxy-3'-methylbenzophenone (Compound J)

Employing the same general procedure as for the preparation 5-bromo-2-methoxy-4'-methylbenzophenone (Compound H), 1.0 mL (1.5 g, 8.0 mmol) of 4-bromoanisole was converted into the title compound using 0.5 g (4.0 mmol) of aluminum chloride, 1.3 mL (1.5 g, 9.6 mmol) of m-toluoyl chloride and 20 mL of dichloromethane. Purification by flash chromatography (silica, 10% ethyl acetate in hexane) gave the title compound as a white solid.

PMR (CDCl$_3$): δ 2.40 (3H, s), 3.72 (3H, s), 6.88 (1H, d, J=8.8 Hz), 7.29–7.36 (1H, m), 7.36–7.42 (1H, m), 7.43 (1H, d, J=2.5 Hz), 7.52–7.58 (2H, m), 7.65 (1H, br s).

5-Bromo-2-hydroxy-4'-methylbenzophenone (Compound K)

To a solution of 190 mg (0.6 mmol) of 5-bromo-2-methoxy-4'-methylbenzophenone (Compound H) in 15 mL of dichloromethane was added 0.9 mL (0.9 mmol) of boron tribromide (1M in dichloromethane) at ambient temperature. The orange solution was stirred at ambient temperature for 3 hours under a blanket of argon. The reaction mixture was cooled to −78° C., quenched with methanol and then extracted between ethyl acetate and sat. NaHCO$_3$ (aq.) solution. The layers were separated and the organic phase was dried over MgSO$_4$, filtered and concentrated in vacuo to give a pale yellow solid. Purification by flash chromatography (silica, 5% ethyl acetate in hexane) gave the title compound as a white solid.

PMR (CDCl$_3$): δ 2.47 (3H, s), 6.97 (1H, d, J=8.8 Hz), 7.33 (2H, d, J=8.2 Hz), 7.54–7.62 (3H, m), 7.72 (1H, d, J=2.5 Hz), 11.93 (1H, s).

5-Bromo-2-hydroxy-3'-methylbenzophenone (Compound L)

Employing the same general procedure as for the preparation 5-bromo-2-hydroxy-4'-methylbenzophenone (Compound K), 533 mg (1.7 mmol) of 5-bromo-2-methoxy-3'-methylbenzophenone (Compound J) was converted into the title compound using 2.6 mL (2.6 mmol) of boron tribromide (1M in dichloromethane) and 15 mL of dichloromethane. Purification by flash chromatography (silica, 10% ethyl acetate in hexane) gave the title compound as a white solid.

PMR (CDCl$_3$): δ 2.45 (3H, s), 6.98 (1H, d, J=8.9 Hz), 7.36–7.52 (4H, m), 7.58 (1H, dd, J=2.4, 8.9 Hz), 7.70 (1H, d, J=2.4 Hz), 11.94 (1H, s).

5-Bromo-2-hydroxy-4-methyl-4'-methylbenzophenone (Compound M)

Employing the same general procedure as for the 5-bromo-2-hydroxy-4'-methylbenzophenone (Compound K), 319 mg (1.0 mmol) of 5-bromo-2-methoxy-4-methyl-4'-methylbenzophenone (Compound I) was converted into the title compound using 2.4 mL (2.4 mmol) of boron tribromide (1M in dichloromethane) and 10 mL of dichloromethane. Purification by flash chromatography (silica, 10% ethyl acetate in hexane) gave the title compound as a pale yellow solid.

PMR (CDCl$_3$): δ 2.42 (3H, s), 2.46 (3H, s), 6.97 (1H, s), 7.33 (1H, d, J=8.0 Hz), 7.58 (1H, d, J=8.0 Hz), 7.74 (1H, s), 11.93 (1H, s).

4-Bromo-2-[(1-m-tolyl)vinyl]phenol (Compound N)

To a cold solution (−78° C.) of 99 mg (0.3 mmol) of 5-bromo-2-hydroxy-3'-methylbenzophenone (Compound L) in 5 mL of tetrahydrofuran (under a blanket of argon) was added 1.0 mL (3.0 mmol) of methyl magnesium chloride (3M in tetrahydrofuran). With the addition, the solution turned yellowish-orange in color. The −78° C. bath was removed and the solution was allowed to warm to ambient temperature and stirred for 2 hours. The reaction mixture was concentrated in vacuo, extracted between ethyl acetate and sat. NH$_4$Cl (aq.) solution and the layers were separated. The organic phase was washed with water and brine, dried over MgSO$_4$, filtered and concentrated in vacuo to give crude 4-bromo-2-[(1-m-tolyl-1-hydroxy)ethyl]phenol as a yellow oil. The crude alcohol was dissolved in 2 mL of toluene, placed under a blanket of argon and 5.9 mg of p-toluene sulfonic acid monohydrate was added. The resultant mixture was heated at 70° C. for 45 minutes, cooled to ambient temperature and purified by flash chromatography (silica, 5% ethyl acetate in hexane) to give the title compound as a clear, colorless oil.

PMR (CDCl$_3$): δ 2.34 (3H, s), 5.09 (1H, s), 5.40 (1H, br s), 5.84 (1H, br s), 6.83 (1H, d, J=8.6 Hz), 7.11–7.20 (3H, m), 7.22–7.30 (1H, m), 7.35 (1H, dd, J=2.5, 8.6 Hz).

2-Acetoxy-5-bromo-4'-methylbenzophenone (Compound O)

To a yellow solution of 229 mg (0.8 mmol) of 5-bromo-2-hydroxy-4'-methylbenzophenone (Compound K) in 15 mL of dichloromethane (under a blanket of argon) was added 0.07 mL (69 mg, 0.9 mmol) of pyridine followed by 0.07 mL (74 mg, 0.9 mmol) of acetyl chloride. The resultant reaction mixture was stirred at ambient temperature overnight (16.75 hours), poured into 10% HCl (aq.) solution and extracted with ethyl acetate. The layers were separated and the aqueous phase was washed with ethyl acetate. The organic phases were combined and then sequentially washed with sat. NaHCO$_3$ (aq.) solution, water and brine, dried over MgSO$_4$, filtered and concentrated in vacuo to give a yellow oil. Purification by flash chromatography (silica, 20% ethyl acetate in hexane) gave the title compound as a clear, colorless oil.

PMR (CDCl$_3$): δ 1.95 (3H, s), 2.43 (3H, s), 7.09 (1H, d, J=8.1 Hz), 7.27 (2H, d, J=approximately 8 Hz), 7.60–7.70 (4H, m).

5-Bromo-2-methoxymethoxyacetophenone (Compound P)

To a cold solution (0° C.) of 4.5 g (21.0 mmol) of 5-bromo-2-hydroxyacetophenone (Compound F) in 160 mL of dichloromethane (under a blanket of argon) was added 22 mL (16.3 g, 126.3 mmol) of N,N-diisopropylethylamine followed by 2.6 mL (2.8 g, 34.2 mmol) of chloromethyl methyl ether and 52 mg of tetrabutylammonium iodide. The resultant yellow solution was heated to reflux in an oil bath (45° C.) overnight (14.75 hours), cooled to ambient temperature, concentrated in vacuo and then extracted and partitioned between ethyl acetate and sat. NaHCO$_3$ (aq.) solution. The layers were separated and the organic phase was washed with water and brine, dried over MgSO$_4$, filtered and concentrated in vacuo to a yellow oil. Purification by flash chromatography (silica, 10% ethyl acetate in hexane) gave the title compound as a yellow oil.

PMR (CDCl$_3$): δ 2.62 (3H, s), 3.51 (3H, s), 5.26 (2H, s), 7.10 (1H, d, J=8.7 Hz), 7.51 (1H, dd, J=2.6, 8.7 Hz), 7.81 (1H, d, J=2.6 Hz).

5-Bromo-2-methoxymethoxy-4-methyl-4'-methylbenzophenone (Compound Q)

Employing the same general procedure as for the preparation 5-bromo-2-methoxymethoxyacetophenone (Compound P), 250 mg (0.8 mmol) 5-bromo-2-hydroxy-4-methyl-4'-methylbenzophenone (Compound M) was converted into the title compound using 0.2 mL (0.2 g, 2.5 mmol) of chloromethyl methyl ether, 0.85 mL (0.6 g, 4.9 mmol) of N,N-diisopropylethylamine, 10 mL of dichloromethane and a catalytic amount of tetrabutylammonium iodide (<5 mg). Purification by flash chromatography (silica, 10% ethyl acetate in hexane) gave the title compound as a white solid.

PMR (CDCl$_3$): δ 2.42 (3H, s), 2.44 (3H, s), 3.32 (3H, s), 5.03 (2H, s), 7.11 (1H, s), 7.24 (2H, d, J=8.2 Hz), 7.49 (1H, s), 7.72 (2H, d, J=8.2 Hz).

4-Bromo-2-[(1-p-tolyl)vinyl]phenol (Compound R)

To a solution of 2.2 g (8.5 mmol) of 5-bromo-2-methoxymethoxyacetophenone (Compound P) in 25 mL of ethyl ether (under a blanket of argon) was added 25.5 mL (25.5 mmol) of p-tolylmagnesium bromide (1M in ether) via syringe. The yellow solution effervesced as the Grignard reagent was being added. The reaction mixture was allowed to stir at ambient temperature for 17 hours, poured into 75 mL of ice water and extracted and partitioned between 10% HCl (aq.) solution and ethyl ether. The layers were separated and the organic phase was washed with water and brine, dried over MgSO$_4$, filtered and concentrated in vacuo to give an inseparable mixture of tertiary alcohols (4-bromo-2-[(1-hydroxy-1-p-tolyl)ethyl]phenol and 4-bromo-1-methoxymethoxy-2-[(1-hydroxy-1-p-tolyl)ethyl]benzene (approximately 2.5 to 1 ratio, respectively) following flash chromatography. The mixture was dissolved in 15 mL of ethanol (under a blanket of argon) and 5 mL of 10% HCl (aq) solution was added. The resultant reaction mixture was stirred at ambient temperature for 4 hours, heated in an oil bath (90° C.) for 2 hours, cooled to ambient temperature and stirred overnight (14 hours). The reaction mixture was concentrated in vacuo, extracted and partitioned between ethyl acetate and sat. NaHCO$_3$ (aq.) solution and the layers were separated. The organic phase was washed with water and brine, dried over MgSO$_4$, filtered and concentrated in vacuo to a yellow oil. Purification by flash chromatography (silica, 10% ethyl acetate in hexane) gave the title compound as a clear oil.

PMR (CDCl$_3$): δ 2.35 (3H, s), 5.15 (1H, s), 5.35 (1H, br s), 5.81 (1H, br s), 6.81 (1H, d, J=8.6 Hz), 7.15 (2H, d, J=8.2 Hz), 7.23 (2H, d, J=8.2 Hz), 7.27 (1H, d, J=2.5 Hz), 7.33 (1H, dd, J=2.5, 8.6 Hz).

4-Bromo-1-isopropoxy-2-[(1-p-tolyl)vinyl]benzene (Compound S)

To a cold solution (0° C.) of 125 mg (0.4 mmol) of 4-bromo-2-[(1-p-tolyl)vinyl]phenol (Compound R) in 5 mL of tetrahydrofuran was added 125 mg (0.5 mmol) of triphenylphosphine and 0.04 mL (31 mg, 0.5 mmol) of isopropanol followed by 0.07 mL (82 mg, 0.5 mmol) of diethylazodicarboxylate. The dark yellow solution was removed from the ice bath, allowed to warm to ambient temperature on its own and stirred overnight (22.5 hours). The reaction mixture was concentrated in vacuo to a gummy yellow solid. Purification by flash chromatography (silica, 1% ethyl acetate in hexane) gave the title compound as a yellow oil.

PMR (CDCl$_3$): δ 0.98 (6H, d, J=6.1 Hz), 2.33 (3H, s), 4.30 (1H, heptet, J=6.1 Hz), 5.25 (1H, d, J=1.3 Hz), 5.58 (1H, d, J=1.3 Hz), 6.74 (1H, d, J=8.6 Hz), 7.07 (2H, d, J=8.2 Hz), 7.14 (2H, d, J=8.2 Hz), 7.36 (1H, dd, J=2.5, 8.6 Hz), 7.39 (1H, d, J=2.5 Hz).

4-Bromo-1-isopropoxy-2-[(1-m-tolyl)vinyl]phenol (Compound T)

Employing the same general procedure as for the preparation of 4-bromo-1-isopropoxy-2-[(1-p-tolyl)vinyl]benzene (Compound S), 81.5 mg (0.3 mmol) of 4-bromo-2-[(1-m-tolyl)vinyl]phenol (Compound N) was converted into the title compound using 164 mg (0.6 mmol) of triphenylphosphine, 0.10 mL (108 mg, 0.6 mmol) of diethylazodicarboxylate, 0.05 mL (39 mg, 0.6 mmol) of isopropanol and 3 mL of tetrahydrofuran. The reaction was sluggish necessitating addition (after 23 hours of stirring at ambient temperature) of another equivalent of reagents (initially only ½ of the above amounts were added) and stirring for 4 additional days. Purification by flash chromatography (silica, 10% ethyl acetate in hexane) gave the title compound as a pink oil.

PMR (CDCl$_3$): δ 0.97 (6H, d, J=6.0 Hz), 2.30 (3H, s), 4.31 (1H, heptet, J=6.0 Hz), 5.29 (1H, d, J=1.4 Hz), 5.59 (1H, d, J=1.4 Hz), 6.73 (1H, d, J=8.6 Hz), 7.02–7.10 (3H, m), 7.12–7.20 (1H, m ), 7.36 (1H, dd, J=2.6, 8.6 Hz), 7.40 (1H, d, J=2.6 Hz).

4-Bromo-1-tert-butyldimethylsilanyloxy-2-[(1-p-tolyl)vinyl]benzene (Compound U)

To a solution of 82 mg (0.3 mmol) of 4-bromo-2-[(1-p-tolyl)vinyl]phenol (Compound R) in 3 mL of dichloromethane (under a blanket of argon) was added 0.05 mL (36 mg, 0.34 mmol) of triethylamine followed by 0.3 mL (0.3 mmol) of ten-butyldimethylsilylchloride (1M in dichloromethane). The resultant yellow solution was stirred at ambient temperature overnight (23.7 hours), concentrated in vacuo and purified by flash chromatography (silica, 100% hexane) to give the title compound as a clear, colorless oil.

PMR (CDCl$_3$): δ 0.03 (6H, s), 0.71 (9H, s), 2.32 (3H, s), 5.22 (1H, br s), 5.69 (1H, br s), 6.69 (1H, d, J=8.5 Hz), 7.07 (2H, d, J=8.2 Hz), 7.16 (2H, d, J=8.2 Hz), 7.30 (1H, dd, J=2.6, 8.5 Hz), 7.34 (1H, d, J=2.56 Hz).

4-Bromo-2-[(1-p-tolyl)vinyl]phenyl acetate (Compound V)

To a solution of 1.3 g (4.6 mmol) of 4-bromo-2-[(1-p-tolyl)vinyl]phenol (Compound R) in 15 mL of dichloromethane (under a blanket of argon) was added 0.77 mL (0.6 g, 5.6 mmol) of triethylamine and 0.4 mL (0.4 g, 5.6 mmol) of acetyl chloride. A white precipitate immediately formed upon addition of acetyl chloride. The reaction mixture was stirred at ambient temperature for 14.5 hours and then concentrated in vacuo. Purification by flash chromatography (silica, 10% ethyl acetate in hexane) gave the title compound as a clear, colorless oil.

PMR (CDCl$_3$): δ 2.34 (3H, s), 5.29 (1H, br s), 5.64 (1H, d, J=1.1 Hz), 6.96 (1H, d, J=8.6 Hz), 7.08–7.17 (4H, m), 7.47 (1H, dd, J=2.5, 8.6 Hz), 7.51 (1H, d, J=2.5 Hz).

2-Methoxy-5-trimethylsilanylethynyl acetophenone (Compound W)

To a sparged solution (a stream of argon was bubbled vigorously into the solution for several minutes) of diethylamine (5 mL) in a pressure tube vessel was added a solution of 1.85 g (8.1 mmol) of 5-bromo-2-methoxyacetophenone (Compound G) in 20 ml of diethylamine. After sparging with argon for 5 minutes, 0.4 g (2.0 mmol) of cuprous iodide was added to the solution and the resultant mixture was sparged with argon for 2 minutes. To this reaction mixture was then added 1.4 g (2.0 mmol) of bis(triphenylphosphine) palladium(II) chloride. After sparging with argon for 3 minutes, 4.3 mL (40.4 mmol) of trimethylsilyl acetylene was added to the reaction mixture. The pressure tube was then sealed and heated in an oil bath (55° C.) for 5 days. The reaction mixture was filtered through celite and washed with ethyl ether (400 mL). The filtrate was extracted with water (3×200 mL-portions) and brine, dried over MgSO$_4$, filtered and concentrated in vacuo to give a dark brown residue. Purification by flash chromatography (preabsorbed onto silica with chloroform, 10% ethyl acetate in hexane) gave the title compound as a yellow solid.

PMR (CDCl$_3$): δ 0.24 (9H, s), 2.01 (2H, t, J=7.1 Hz), 2.59 (3H, s), 3.92 (3H, s), 6.90 (1H, d, J=8.6 Hz), 7.55 (1H, dd, J=2.2, 8.6 Hz), 7.84 (1H, d, J=2.2 Hz).

2-Acetoxy-5-trimethylsilanylethynyl-4'-methylbenzophenone (Compound X)

Employing the same general procedure as for the preparation of 2-methoxy-5-trimethylsilanylethynyl acetophenone (Compound W), 228.5 mg (0.7 mmol) of 2-acetoxy-5-bromo-4'-methylbenzophenone (Compound O) was converted into the title compound using 120 mg (0.2 mmol) of bis(triphenylphosphine)palladium (II) chloride, 33 mg (0.2 mmol) of cuprous iodide, 0.73 mL (670 mg, 6.9 mmol) of trimethylsilyl acetylene and 10 mL of triethylamine (heated at 75° C.). Purification by flash chromatography (silica, 5% ethyl acetate in hexane) gave the title compound as an oil.

PMR (CDCl$_3$): δ 0.23 (9H, s), 1.98 (3H, s), 2.43 (3H, s), 7.14 (1H, d, J=8.2 Hz), 7.27 (2H, d, J=8.1 Hz), 7.57–7.63 (2H, m), 7.67 (2H, d, J=8.1 Hz).

4-Trimethylsilanylethynyl-2-[(1-p-tolyl)vinyl]phenyl acetate (Compound Y)

Employing the same general procedure as for the preparation of 2-methoxy-5-trimethylsilanylethynyl acetophenone (Compound W), 515 mg (1.6 mmol) of 4-bromo-2-[(1-p-tolyl)vinyl]phenyl acetate (Compound V) was converted into the title compound using 219 mg (0.3 mmol) of bis(triphenylphosphine)palladium (II) chloride, 58 mg (0.3 mmol) of cuprous iodide, 1.66 mL (1.5 g, 15.6 mmol) of trimethylsilyl acetylene and 10 mL of triethylamine (heated at 75° C.). Purification by flash chromatography (silica, 5% ethyl acetate in hexane) gave the title compound as a tan solid.

PMR (CDCl$_3$): δ 0.27 (9H, s), 1.80 (3H, s), 2.36 (3H, s), 5.31 (1H, br s), 5.65 (1H, br s), 7.04 (1H, d, J=8.3 Hz), 7.10–7.19 (4H, m), 7.47 (1H, dd, J=2.0, 8.3 Hz), 7.52 (1H, d, J=2.0 Hz).

3-Trimethylsilanylethynyl acetophenone (Compound Z)

Employing the same general procedure as for the preparation of 2-methoxy-5-trimethylsilanylethynyl acetophenone (Compound W), 0.66 mL (1.0 g, 5.0 mmol) of 3-bromoacetophenone was converted into the title compound using 0.9 g (1.3 mmol) of bis(triphenylphosphine) palladium (II) chloride, 0.2 g (1.0 mmol) of cuprous iodide, 5.4 mL (5.0 g, 50.7 mmol) of trimethylsilyl acetylene and 12 mL of triethylamine (heated at 75° C.). Purification by flash chromatography (silica, 5% ethyl acetate in hexane) gave the title compound as a yellow oil.

PMR (CDCl$_3$): δ 0.27 (9H, s), 2.61 (3H, s), 7.38–7.44 (1H, m), 7.62–7.67 (1H, m), 7.84–7.86 (1H, m), 8.10–8.25 (1H, m).

2-Methoxymethoxy-4-methyl-5-trimethylsilanylethynyl-4'-methylbenzophenone (Compound A1)

Employing the same general procedure as for the preparation of 2-methoxy-5-trimethylsilanylethynyl acetophenone (Compound W), 264 mg (0.76 mmol) of 5-bromo-2-methoxymethoxy-4-methyl-4'-methylbenzophenone (Compound Q) was converted into the title compound using 133 mg (0.2 mmol) of bis(triphenylphosphine)palladium (II) chloride, 36 mg (0.2 mmol) of cuprous iodide, 0.8 mL (0.7 g, 7.6 mmol) of trimethylsilyl acetylene and 10 mL of triethylamine (heated at 75° C.). Purification by flash chromatography (silica, 5% ethyl acetate in hexane) gave the title compound as a yellow oil.

PMR (CDCl$_3$): δ 0.23 (9H, s), 2.41 (3H, s), 2.48 (3H, s), 3.32 (3H, s), 5.06 (2H, s), 7.04 (1H, s), 7.21 (2H, d, J=8.2 Hz), 7.43 (1H, s), 7.70 (2H, d, J=8.2 Hz).

1-Isopropoxy-4-trimethylsilanylethyyl-2-[(1-p-tolyl)vinyl]benzene (Compound B1)

Employing the same general procedure as for the preparation of 2-methoxy-5-trimethylsilanylethynyl acetophenone (Compound W), 64 mg (0.2 mmol) of 4-bromo-1-isopropoxy-2-[(1-p-tolyl)vinyl]benzene (Compound S) was converted into the title compound using 33.5 mg (0.05 mmol) of bis(triphenylphosphine)palladium (11) chloride, 9 mg (0.05 mmol) of cuprous iodide, 0.3 mL (0.3 g, 2.8 mmol) of trimethylsilyl acetylene and 5 mL of triethylamine (heated at 75° C.). Purification by flash chromatography (silica, 2% ethyl acetate in hexane) gave the title compound as a yellow oil.

PMR (CDCl$_3$): δ 0.26 (9H, s), 0.99 (6H, d, J=6.0 Hz), 2.34 (3H, s), 4.37 (1H, heptet, J=6.0 Hz), 5.26 (1H, d, J=1.5 Hz), 5.58 (1H, d, J=1.5 Hz), 6.79 (1H, d, J=8.4 Hz), 7.05–7.18 (4H, m), 7.38–7.46 (2H, m).

1-Isopropoxy-4-trimethylsilanylethynyl-2-[(1-m-tolyl)vinyl]benzene (Compound C1)

Employing the same general procedure as for the preparation of 2-methoxy-5-trimethylsilanylethynyl acetophenone (Compound W), 37 mg (0.1 mmol) of 4-bromo-1-isopropoxy-2-[(1-m-tolyl)vinyl]benzene (Compound T) was converted into the title compound using 20 mg (0.03 mmol) of bis(triphenylphosphine)palladium (II) chloride, 6 mg (0.03 mmol) of cuprous iodide, 0.12 mL (111 mg, 1.1 mmol) of trimethylsilyl acetylene and 3 mL of triethylamine (heated at 75° C.). Purification by flash chromatography (silica, 1% ethyl acetate in hexane) gave the title compound as a yellow oil.

PMR (CDCl$_3$): δ 0.24 (9H, s), 0.95 (6H, d, J=6.1 Hz), 2.29 (3H, s), 4.37 (1H, heptet, J=6.1 Hz), 5.28 (1H, d, J=1.5 Hz), 5.57 (1H, d, J=1.5 Hz), 6.77 (1H, d, J=8.4 Hz), 7.00–7.10 (3H, m), 7.10–7.20 (1H, m), 7.40 (1H, dd, J=2.2, 8.4 Hz), 7.43 (1H, d, J=2.2 Hz).

1-tert-Butyldimethylsilanyloxy-4-trimethylsilanylethynyl-2-[(1-p-tolyl)vinyl]benzene (Compound D1)

Employing the same general procedure as for the preparation of 2-methoxy-5-trimethylsilanylethynyl acetophenone (Compound W), 43.4 mg (0.1 mmol) of 1-tert-butyldimethylsilanyloxy-4-bromo-2-[(1-p-tolyl)vinyl] benzene (Compound U) was converted into the title compound using 19 mg (0.03 mmol) of bis (triphenylphosphine)palladium (II) chloride, 6.8 mg (0.03 mmol) of cuprous iodide, 0.11 mL (101 mg, 1.1 mmol) of trimethylsilyl acetylene and 4 mL of triethylamine (heated at 75° C.). Purification by flash chromatography (silica, 2% ethyl acetate in hexane) gave the title compound as a yellow oil.

PMR (CDCl$_3$): δ 0.04 (6H, s), 0.24 (9H, s), 0.71 (9H,s), 2.32 (3H, s), 5.22 (1H, d, J=1.3 Hz), 5.68 (1H, d, J=1.3 Hz), 6.74 (1H, d, J=8.3 Hz), 7.02–7.10 (2H, m), 7.12–7.20 (2H, m), 7.33 (1H, dd, J=2.2, 8.3 Hz), 7.38 (1H, d, J=2.2 Hz).

5-Ethynyl-2-methoxyacetophenone (Compound E1)

To a solution of 990 mg (4.0 mmol) of 2-methoxy-5-trimethylsilanylethynylacetophenone (Compound W) in 100 mL of methanol was added 144 mg (1.0 mmol) of potassium carbonate. The mixture was stirred for 2.5 hours at ambient temperature (under a blanket of argon). The dark brown solution was concentrated in vacuo to a brown residue, diluted with dichloromethane (5 mL) and sat. NaHCO$_3$ (aq.) solution (100 mL), and then stirred at ambient temperature for approx. 30 minutes. The mixture was extracted between dichloromethane and water, the layers were separated and the aqueous phase was washed with dichloromethane. The organic phases were combined and sequentially washed with water and brine, dried over MgSO$_4$, filtered and concentrated in vacuo. Purification by column chromatography (silica, 10% ethyl acetate in hexane) yielded the title compound as a white solid.

PMR (CDCl$_3$): δ 2.60 (3H, s), 3.01 (1H, s), 3.93 (3H, s), 6.92 (1H, d, J=8.5 Hz), 7.58 (1H, dd, J=2.1, 8.5 Hz), 7.86 (1H, d, J=2.1 Hz).

5-Ethynyl-2-hydroxy-4'-methylbenzophenone (Compound F1)

To a solution of 100 mg (0.3 mmol) of 2-acetoxy-5-trimethylsilanylethynyl-4'-methylbenzophenone (Compound X) in 5 mL of tetrahydrofuran (under a blanket of argon) was added 0.86 mL (0.86 mmol) of tetrabutylammonium fluoride (1M in tetrahydrofuran). The resultant yellow solution was stirred at ambient temperature for 30 minutes, diluted with water (1 mL), extracted between ethyl ether and 10% HCl (aq.) solution, the layers separated and the aqueous phase washed with ethyl ether. The organic phases were combined, dried over MgSO$_4$, filtered and concentrated in vacuo. Purification by flash chromatography (silica, 3% ethyl acetate in hexane) gave the title compound as an oil.

PMR (CDCl$_3$): δ 2.46 (3H, s), 2.96 (1H, s), 7.03 (1H, d, J=8.6 Hz), 7.33 (2H, d, J=7.8 Hz), 7.58–7.64 (3H, m), 7.78 (1H, d, J=2.0 Hz), 12.17 (1H, s).

5-Ethynyl-2-methoxmethoxy-4'-methylbenzophenone (Compound G1)

Employing the same general procedure as for the preparation of 5-bromo-2-methoxymethoxyacetophenone (Compound P), 70 mg (0.3 mmol) of 5-ethynyl-2-hydroxy- 4'-methylbenzophenone (Compound F1) was converted into the title compound using 0.3 mL (1.7 mmol) of N,N-diisopropylethylamine, 0.7 mL (0.9 mmol) of chloromethyl methyl ether, a catalytic amount of tetrabutylammonium iodide (<5 mg) and 5 mL of dichloromethane. The yellow residue obtained was of sufficient purity to be used without further purification.

PMR (CDCl$_3$): δ 2.41 (3H, s), 3.01 (1H, s), 3.31 (3H, s), 5.07 (2H, s), 7.16 (1H, d, J=8.7 Hz), 7.23 (2H, d, J=approximately 8 Hz), 7.46 (1H, d, J=2.1 Hz), 7.55 (1H, dd, J=2.1, 8.7 Hz), 7.71 (2H, d, J=approximately 8 Hz).

4-Ethynyl-2-[(1-p-tolyl)vinyl]phenyl acetate (Compound H1) and 4-Ethynyl-2-[(1-p-tolyl)vinyl]phenol (Compound I1)

Employing the same general procedure as for the preparation of 5-ethynyl-2-hydroxy-4'-methylbenzophenone (Compound F1), 500 mg (1.4 mmol) of 4-trimethylsilanylethynyl-2-[(1-p-tolyl)vinyl]phenyl acetate (Compound Y) was converted into the title compounds using 3.2 mL (3.2 mmol) of tetrabutylammonium fluoride (1M in tetrahydrofuran) and 20 mL of tetrahydrofuran. Purification by flash chromatography (silica, 10% ethyl acetate in hexane) gave the title compounds as clear oils in a 1:1 ratio.

PMR: 4-Ethynyl-2-[(1-p-tolyl)vinyl]phenyl acetate (Compound H1): (CDCl$_3$): δ 1.78 (3H, s), 3.07 (1H, s), 5.29 (1H, br s), 5.63 (1H, br s), 7.03 (1H, d, J=8.2 Hz), 7.10–7.16 (4H, m), 7.47 (1H, dd, J=2.0, 8.2 Hz), 7.52 (1H, d, J=2.0 Hz).

PMR: 4-Ethynyl-2-[(1-p-tolyl)vinyl]phenol (Compound I1): (CDCl$_3$): δ 2.36 (3H, s), 2.98 (1H, s), 5.31 (1H, s), 5.37 (1H, br s), 5.84 (1H, br s), 6.89 (1H, d, J=8.4 Hz), 7.20, (2H, d, J=8 Hz), 7.24 (2H, d, J=8 Hz), 7.32 (1H, d, J=2.1 Hz), 7.39 (1H, dd, J=2.1, 8.4 Hz).

4-Ethynyl-1-methoxymethoxy-2-[(1-p-tolyl)vinyl]benzene (Compound J1)

Employing the same general procedure as for the preparation of 5-bromo-2-methoxymethoxy acetophenone (Compound P), 109 mg (0.5 mmol) of 4-ethynyl-2-[(1-p-tolyl)vinyl]phenol (Compound I1) was converted into the title compound using 0.11 mL (117 mg, 1.45 mmol) of chloromethyl methyl ether, 0.49 mL (360 mg, 2.8 mmol) of N,N-diisopropylethylamine, a catalytic amount of tetrabutylammonium iodide (<5 mg) and 5 mL of dichloromethane. Purification by flash chromatography (silica, 10% ethyl acetate in hexane) gave the title compound as a clear, colorless oil.

PMR (CDCl$_3$): δ 2.32 (3H, s), 3.01 (1H, s), 3.17 (3H, s), 4.96 (2H, s), 5.25 (1H, s), 5.68 (1H, br s), 7.00–7.10 (3H, m), 7.17 (2H, d, J=approximately 8 Hz), 7.41–7.46 (2H, m).

3-Ethynylacetophenone (Compound K1)

Employing the same general procedure as for the preparation of 5-ethynyl-2-methoxyacetophenone (Compound E1), 1.1 g (5.0 mmol) of 3-trimethylsilanylethynyl acetophenone (Compound Z) was converted into the title compound using 172 mg (1.25 mmol) of potassium carbonate and 10 mL of methanol. Purification by flash chromatography (silica, 10% ethyl acetate in hexane) gave the title compound as a yellow solid.

PMR (CDCl$_3$): δ 2.61 (3H, s), 3.15 (1H, s), 7.40–7.50 (1H, m), 7.65–7.68 (1H, m), 7.90–7.95 (1H, m), 8.05–8.08 (1H, m).

5-Ethynyl-2-methoxymethoxy-4-methyl-4'-methylbenzophenone (Compound L1)

Employing the same general procedure as for the preparation of 5-ethynyl-2-methoxyacetophenone (Compound E1), 260 mg (0.8 mmol) of 2-methoxymethoxy-4-methyl-5-trimethylsilanylethynyl-4'-methylbenzophenone (Compound A1) was converted into the title compound using 26 mg (0.2 mmol) of potassium carbonate and 5 mL of methanol. Purification by flash chromatography (silica, 5% ethyl acetate in hexane) gave the title compound as a white solid.

PMR (CDCl$_3$): δ 2.41 (3H, s), 2.50 (3H, s), 3.22 (1H, s), 3.32 (3H, s), 5.07 (2H, s), 7.06 (1H, s), 7.23 (2H, d, J=8.4 Hz), 7.46 (1H, s), 7.71 (2H, d, J=8.4 Hz).

4-Ethynyl-1-isopropoxy-2-[(1-p-tolyl)vinyl]benzene (Compound M1)

Employing the same general procedure as for the preparation of 5-ethynyl-2-methoxyacetophenone (Compound E1), 53 mg (0.15 mmol) 1-isopropoxy-4-trimethylsilanylethynyl-2-[(1-p-tolyl)vinyl]benzene (Compound B1) was converted into the title compound using 8 mg (0.06 mmol) of potassium carbonate and 4 mL of methanol. Purification by flash chromatography (silica, 5% ethyl acetate in hexane) gave the title compound as a yellow oil.

PMR (CDCl$_3$): δ 0.99 (6H, d, J=6.0 Hz), 2.33 (3H, s), 3.00 (1H, s), 4.37 (1H, heptet, J=6.0 Hz), 5.25 (1H, d, J=1.5 Hz), 5.57 (1H, d, J=1.5 Hz), 6.79 (1H, d, J=8.7 Hz), 7.06 (2H, d, J=8.2 Hz), 7.14 (2H, d, J=8.2 Hz), 7.40–7.45 (2H, m).

4-Ethynyl-1-isopropoxy-2-[(1-m-tolyl)vinyl]benzene (Compound N1)

Employing the same general procedure as for the preparation of 5-ethynyl-2-methoxyacetophenone (Compound E1), 22 mg (0.07 mmol) 1-isopropoxy-4-trimethylsilanylethynyl-2-[(1-m-tolyl)vinyl]benzene (Compound C1) was converted into the title compound using 3 mg (0.02 mmol) of potassium carbonate and 3 mL of methanol. Purification by flash chromatography (silica, 1% ethyl acetate in hexane) gave the title compound as a yellow oil.

PMR (CDCl$_3$): δ 0.98 (6H, d, J=6.0 Hz), 2.30 (3H, s), 3.01 (1H, s), 4.37 (1H, heptet, J=6.0 Hz), 5.29 (1H, br s), 5.58 (1H, d, J=1.5 Hz), 6.79 (1H, d, J=8.5 Hz), 7.00–7.10 (3H, m), 7.10–7.20 (1H, m), 7.40–7.50 (2H, m).

1-tert-Butyldimethylsilanyloxy-4-ethynyl-2-[(1-p-tolyl)vinyl]benzene (Compound O1)

Employing the same general procedure as for the preparation of 5-ethynyl-2-methoxyacetophenone (Compound E1), 25 mg (0.06 mmol) 1-tert-butyldimethylsilanyloxy-4-trimethylsilanylethynyl-2-[(1-p-tolyl)vinyl]benzene (Compound D1) was converted into the title compound using 4 mg (0.03 mmol) of potassium carbonate and 1 mL of ethanol. Purification by flash chromatography (silica, 5% ethyl acetate in hexane) gave the title compound as a yellow oil.

PMR (CDCl$_3$): δ 0.05 (6H, s), 0.71 (9H, s), 2.31 (3H, s), 3.00 (1H, s), 5.22 (1H, br s), 5.68 (1H, br s), 6.75 (1H, d, J=8.2 Hz), 7.06 (2H, d, J=8.2 Hz), 7.16 (2H, d, J=8.2 Hz), 7.35 (1H, dd, J=2.1, 8.2 Hz), 7.38 (1H, d, J=2.1 Hz).

Ethyl 4-[(3'-acetyl-4'-methoxy)phenylethynyl]benzoate (Compound 1)

To a sparged solution of 10 mL of diethylamine (a stream of argon was bubbled vigorously into the solution for several minutes) was added a mixture of 440 mg (2.5 mmol) of 5-ethynyl-2-methoxyacetophenone (Compound E1), 770 mg (2.8 mmol) of ethyl 4-iodobenzoate (Compound A) and 10 mL of diethylamine. After sparging with argon for 5 minutes, 96 mg (0.5 mmol) of cuprous iodide was added to the solution and the resultant mixture was sparged with argon for 3 minutes. The mixture was cooled to 0° C. in an ice bath and then 440 mg (0.6 mmol) of bis (triphenylphosphine)palladium (II) chloride was added. The reaction mixture was stirred at 0° C. for 30 minutes (initial 5 minutes performed under sparging conditions), allowed to warm to ambient temperature and then stirred at ambient temperature for 27 hours. The reaction mixture was filtered through celite, washed with ethyl ether (250 mL) and the collected filtrate washed with water (3×200 mL-portions) and brine (150 mL). The organic phase was dried over $MgSO_4$, filtered and concentrated in vacuo to a solid residue. Purification by flash chromatography (preabsorbed onto silica with chloroform, 10% ethyl acetate in hexane) gave the title compound as a pale yellow solid.

PMR ($CDCl_3$): δ 1.41 (3H, t, J=7.1 Hz), 2.63 (3H, s), 3.96 (3H, s), 4.39 (2H, q, J=7.1 Hz), 6.98 (1H, d, J=8.6 Hz), 7.56 (2H, d, J=8.4 Hz), 7.64 (1H, dd, J=2.2, 8.6 Hz), 7.93 (1H, d, J=2.2 Hz), 8.02 (2H, d, J=8.4 Hz).

4-[(3'-Acetyl-4'-methoxy)phenylethynyl]benzoic acid (Compound 2)

To a solution of 102.5 mg (0.3 mmol) of ethyl 4-[(3'-acetyl-4'-methoxy)phenylethynyl]benzoate (Compound 1) in 15 mL of tetrahydrofuran was added 3.2 mL (3.2 mmol) of LiOH solution (1M in water). The reaction mixture was allowed to stir at ambient temperature for 3 days, concentrated in vacuo, and extracted between hexane and water. The layers were separated and the aqueous phase was diluted with ethyl ether, cooled to 0° C. in an ice bath and acidified with 1N $H_2SO_4$ (aq.) solution to pH 3–4. The solution was diluted with brine and the organic phase was separated. The organic phase was dried over $Na_2SO_4$, filtered and concentrated in vacuo to give the title compound as a white solid.

PMR (DMSO-$d_6$): δ 2.54 (3H, s), 3.93 (3H, s), 7.25 (1H, d, J=9 Hz), 7.65 (2H, d, J=approximately 8 Hz), 7.73–7.78 (2H, m), 7.95 (2H, d, J=approximately 8 Hz).

Ethyl 4-[[4'-methoxymethoxy-3'-(4"-methyl) benzoyl]phenylethynyl]benzoate (Compound 3)

Employing the same general procedure as for the preparation of ethyl 4-[(3'-acetyl-4'-methoxy)phenylethynyl] benzoate (Compound 1), 44 mg (0.2 mmol) of 5-ethynyl-2-methoxymethoxy-4'-methylbenzophenone (Compound G1) was converted into the title compound using 46 mg (0.2 mmol) of ethyl 4-iodobenzoate (Compound A), 22 mg (0.03 mmol) of bis(triphenylphosphine)palladium (II) chloride, 6 mg (0.03 mmol) of cuprous iodide and 6 mL of triethylamine. Purification by flash chromatography (silica, 10–20% ethyl acetate in hexane) gave the title compound as a yellow solid.

PMR ($CDCl_3$): δ 1.40 (3H, t, J=7.1 Hz), 2.42 (3H, s), 3.33 (3H, s), 4.38 (2H, q, J=7.1 Hz), 5.10 (2H, s), 7.22 (1H, d, J=8.6 Hz), 7.25 (2H, d, J=8.2 Hz), 7.52–7.58 (3H, m), 7.61 (1H, dd, J=2.1, 8.6 Hz), 7.74 (2H, d, J=8.3 Hz), 8.01 (2H, d, J=8.3 Hz).

Ethyl 4-[[4'-hydroxy-3'-(4"-methyl)benzoyl] phenylethynyl]benzoate (Compound 4)

To a solution of 34 mg (0.08 mmol) of ethyl 4-[[4'-methoxymethoxy-3'-(4"-methyl)benzoyl]phenylethynyl] benzoate (Compound 3) in 3 mL of ethanol (under a blanket of argon) was added 3 drops of c. HCl via pipet. The reaction mixture was heated to reflux in an oil bath (95° C.) for 35 minutes, cooled to ambient temperature and concentrated in vacuo. The residue was extracted and partitioned between ethyl acetate and sat. $NaHCO_3$ (aq.) solution. The layers were separated and the organic phase was washed with water and brine, dried over $MgSO_4$, filtered and concentrated in vacuo to a yellow solid. Purification by flash chromatography (silica, 10% ethyl acetate in hexane) gave the title compound as a yellow solid.

PMR ($CDCl_3$): δ 1.41 (3H, t, J=7.1 Hz), 2.48 (3H, s), 4.39 (2H, q, J=7.1 Hz), 5.10 (2H, s), 7.09 (1H, d, J=8.7 Hz), 7.36 (2H, d, J=8.0 Hz), 7.54 (2H, d, J=8.5 Hz), 7.63–7.69 (3H, m), 7.83 (1H, d, J=2.1 Hz), 8.01 (2H, d, J=8.5 Hz), 12.22 (1H, s).

4-[[4'-hydroxy-3'-(4"-methyl)benzoyl] phenylethynyl]benzoic acid (Compound 5)

To a solution of 16.5 mg (0.04 mmol) of ethyl 4-[[4'-hydroxy-3'-(4"-methyl)benzoyl]phenylethynyl]benzoate (Compound 4) in 2 mL of ethanol and 0.4 mL of tetrahydrofuran (under a blanket of argon) was added 0.4 mL (0.4 mmol) of NaOH solution (1M in water). The yellow solution was stirred at ambient temperature for 20 hours, concentrated in vacuo, acidified with 0.6 mL of 1N (aq) $H_2SO_4$ solution and then extracted between ethyl ether and brine. The layers were separated and the organic phase was dried over $MgSO_4$, filtered and concentrated in vacuo to a yellow solid. Recrystallization from methanol gave the title compound as a yellow needles.

PMR ($CDCl_3$): δ 2.48 (3H, s), 5.10 (2H, s), 7.09 (1H, d, J=8.7 Hz), 7.37 (2H, d, J=8.1 Hz), 7.57 (2H, d, J=8.4 Hz), 7.63–7.69 (3H, m), 7.84 (1H, d, J=2.1 Hz), 8.06 (2H, d, J=8.4 Hz), 12.23 (1H, s).

Ethyl 4-[[4'-acetoxy-3'-(1-p-tolyl)vinyl] phenylethynyl]benzoate (Compound 6)

Employing the same general procedure as for the preparation of ethyl 4-[(3'-acetyl-4'-methoxy)phenylethynyl] benzoate (Compound 1), 128 mg (0.5 mmol) of 4-ethynyl-2-[(1-p-tolyl)vinyl]phenyl acetate (Compound H1) was converted into the title compound using 128 mg (0.5 mmol) of ethyl 4-iodobenzoate (Compound A), 65 mg (0.09 mmol) of bis(triphenylphosphine)palladium (II) chloride, 17 mg (0.09 mmol) of cuprous iodide and 6 mL of triethylamine. Purification by flash chromatography (silica, 10% ethyl acetate in hexane) gave the title compound as a clear, colorless oil which solidified upon standing to a waxy, white solid.

PMR ($CDCl_3$): δ 1.41 (3H, t, J=7.1 Hz), 1.81 (3H, s), 2.35 (3H, s), 4.39 (2H, q, J=7.1 Hz), 5.33 (1H, br s), 5.66 (1H, br s), 7.07–7.19 (5H, m), 7.52–7.60 (4H, m), 8.03 (2H, d, J=8.1 Hz).

Ethyl 4-[[4'-methoxymethoxy-3'-(1-p-tolyl)vinyl] phenylethynyl]benzoate (Compound 7)

Employing the same general procedure as for the preparation of ethyl 4-[(3'-acetyl-4'-methoxy)phenylethynyl] benzoate (Compound 1), 87 mg (0.3 mmol) of 4-ethynyl-1-methoxymethoxy-2-[(1-p-tolyl)vinyl]benzene (Compound J1) was converted into the title compound using 94 mg (0.3 mmol) of ethyl 4-iodobenzoate (Compound A), 42 mg (0.06 mmol) of bis(triphenylphosphine) (11) chloride, 12 mg (0.06 mmol) of cuprous iodide and 6 mL of triethylamine. Purification by flash chromatography (silica, 5% ethyl acetate in hexane) gave the title compound as a white solid.

PMR (CDCl$_3$): δ 1.40 (3H, t, J=7.1 Hz), 2.33 (3H, s), 3.19 (3H, s), 4.39 (2H, q, J=7.1 Hz), 5.00 (2H, s), 5.30 (1H, br s), 5.72 (1H, br s), 7.06–7.12 (3H, m), 7.20 (2H, d, J=8.2 Hz), 7.46–7.52 (2H, m), 7.57 (2H, d, J=8.4 Hz), 8.02 (2H, d, J=8.4 Hz).

4-[[4'-Hydroxy-3'-(1-p-tolyl)vinyl]phenylethynyl] benzoic acid (Compound 8)

Employing the same general procedure as for the preparation of 4-[[4'-hydroxy-3'-(4"-methyl)benzoyl] phenylethynyl]benzoic acid (Compound 5), 84 mg (0.2 mmol) of ethyl 4-[[ 4'-acetoxy-3'-(1-p-tolyl)vinyl] phenylethynyl]benzoate (Compound 6) was converted into the title compound (pale yellow solid) using 2.0 mL (2.0 mmol) of NaOH solution (1M in water), 8 mL of ethanol and 1 mL of tetrahydrofuran.

PMR (Aceton-d$_6$): δ 2.31 (3H, s), 5.32 (1H, d, J=1.4 Hz), 5.77 (1H, br s), 6.96 (1H, d, J=8.3 Hz), 7.12 (2H, d, J=7.9 Hz), 7.23 (2H, d, J=8.3 Hz), 7.35 (1H, d, J=2.1 Hz), 7.44 (1H, dd, J=2.1, 8.4 Hz), 7.62 (2H, d, J=8.4 Hz), 8.03 (2H, d, J=8.4 Hz), 8.52 (1H, br s).

4-[[4'-methoxymethoxy-3'-(1-p-tolyl)vinyl] phenylethyyl]benzoic acid (Compound 9)

Employing the same general procedure as for the preparation of 4-[[4'-hydroxy-3 '-(4"-methyl)benzoyl] phenylethynyl]benzoic acid (Compound 5), 18 mg (0.04 mmol) of ethyl 4-[[4'-methoxymethoxy-3'-(1-p-tolyl)vinyl] phenylethynyl]benzoate (Compound 7) was converted into the title compound using 0.4 mL (0.4 mmol) of NaOH solution (1M in water), 2 mL of ethanol and 0.8 mL of tetrahydrofuran.

PMR (Aceton-d$_6$): δ 2.30 (3H, s), 3.14 (3H, s), 5.05 (2H, s), 5.27 (1H, br s), 5.73 (1H, br s), 7.12 (2H, d, J=7.9 Hz), 7.15–7.22 (3H, m), 7.43 (1H, d, J=2.1 Hz), 7.56 (1H, dd, J=2.1, 8.4 Hz), 7.65 (2H, d, J=8.3 Hz), 8.05 (2H, d, J=8.3 Hz).

Ethyl 4-[[4'-methoxy-3'-(1-hydroxy-1-p-tolyl)ethyl] phenylethynyl]benzoate (Compound 10)

To a cold solution (−78° C.) of 132.5 mg (0.4 mmol) of ethyl 4-[(3'-acetyl-4'-methoxy)phenylethynyl]benzoate (Compound 1) in 5 mL of tetrahydrofuran (under a blanket of argon) was added 0.6 mL (0.6 mmol) of p-tolylmagnesium bromide (IM in ethyl ether). The clear, colorless solution immediately turned orange-reddish in color. The —78° C. bath was removed, the reaction mixture was allowed to slowly warm on its own to ambient temperature, stirred at ambient temperature for 2.25 hours, and concentrated in vacuo. Purification by flash chromatography (silica, 10% ethyl acetate in hexane) gave the title compound as a white solid.

PMR (CDCl$_3$): δ 1.41 (3H, t, J=7.1 Hz), 1.85 (3H, s), 2.31 (3H, s), 3.64 (3H, s), 4.39 (2H, q, J=7.1 Hz), 4.43 (1H, s), 6.86 (1H, d, J=8.5 Hz), 7.07 (2H, d, J=8.1 Hz), 7.19 (2H, d, J=8.1 Hz), 7.50 (1H, dd, J=2.1, 8.5 Hz), 7.59 (2H, d, J=8.4 Hz), 7.67 (1H, d, J=2.1 Hz), 8.03 (2H, d, J=8.4 Hz).

Ethyl 4-[[4'-methoxy-3'-(1-p-tolyl)vinyl] phenylethnyl]benzoate (Compound 11)

To a solution of 40.5 mg (0.1 mmol) of ethyl 4-[[4'-methoxy-3'-(1-hydroxy-1-p-tolyl)ethyl]phenylethynyl] benzoate (Compound 10) in 2 mL of toluene (under a blanket of argon) was added approximately 8 mg of p-toluene sulfonic acid monohydrate. The reaction mixture was heated at 70° C. for 20 minutes, cooled to ambient temperature and then concentrated in vacuo. Purification by flash chromatography (silica, 10% ethyl acetate in hexane) gave the title compound as a white solid.

PMR (CDCl$_3$): δ 1.40 (3H, t, J=7.1 Hz), 2.34 (3H, s), 3.68 (3H, s), 4.38 (2H, q, J=7.1 Hz), 5.28 (1H, d, J=1.3 Hz), 5.73 (1H, br s), 6.89 (1H, d, J=8.6 Hz), 7.09 (2H, d, J=8.2 Hz), 7.19 (2H, d, J=8.2 Hz), 7.45 (1H, d, J=2.1 Hz), 7.50–7.58 (3H, m), 8.01 (2H, d, J=8.5 Hz).

4-[[4'-Methoxy-3'-(1-p-tolyl)vinyl]phenylethynyl] benzoic acid (Compound 12)

Employing the same general procedure as for the preparation of 4-[[4'-hydroxy-3'-(4"-methyl)benzoyl] phenylethynyl]benzoic acid (Compound 5), 25 mg (0.06 mmol) of ethyl 4-[[4'-methoxy-3'-(1-p-tolyl)vinyl] phenylethynyl]benzoate (Compound 11) was converted into the title compound (white solid) using 0.6 mL (0.6 mmol) of NaOH solution (1M in water), 2.5 mL of ethanol and 0.5 mL of tetrahydrofuran.

PMR (Aceton-d$_6$): δ 2.30 (3H, s), 3.69 (3H, s), 5.24 (1H, d, J=1.5 Hz), 5.72 (1H, br s), 7.08–7.16 (3H, m), 7.17 (2H, d, J=8.4 Hz), 7.39 (1H, d, J=2.2 Hz), 7.58 (1H, dd, J=2.2, 8.7 Hz), 7.64 (2H, d, J=8.3 Hz), 8.04 (2H, d, J=8.3 Hz).

4-[[4'-methoxymethoxy-3'-(4"-methyl)benzoyl] phenylethynyl]benzoic acid (Compound 13)

Employing the same general procedure as for the preparation of 4-[[4'-hydroxy-3'-(4"-methyl)benzoyl] phenylethynyl]benzoic acid (Compound 5), 14 mg (0.03 mmol) of ethyl 4-[[4'-methoxymethoxy-3'-(4"-methyl) benzoyl]phenylethynyl]benzoate (Compound 3) was converted into the title compound (white solid) using 0.3 mL (0.3 mmol) of NaOH solution (1M in water), 3.2 mL of ethanol and 0.2 mL of tetrahydrofuran. The white solid obtained was rinsed with 2 mL of 20% ethyl acetate in hexane to give the title compound.

PMR (Aceton-d$_6$): δ 2.41 (3H, s), 3.27 (3H, s), 5.16 (2H, s), 7.31–7.38 (3H, m), 7.53 (1H, d, J=2.1 Hz), 7.64–7.73 (5H, m), 8.05 (2H, d, J=8.4 Hz).

Ethyl 4-[(3'-acethyl-4'-methoxymethoxy) phenylethyl]benzoate (Compound 14)

5-bromo-2-methoxymethoxyacetophenone (Compound P) was converted into the title compound in a step-wise set of reaction conditions resulting in the final isolation of the title compound as a white solid. Employing the same general procedure as for the preparation of 2-methoxy-5-trimethylsilanylethynyl acetophenone (Compound W), 598 mg (2.3 mmol) of 5-bromo-2-methoxymethoxyacetophenone (Compound P) was converted into 2-methoxymethoxy-5-trimethylsilanylethynyl acetophenone using 405 mg (0.6 mmol) of bis (triphenylphosphine)palladium (II) chloride, 90 mg (0.5 mmol) of cuprous iodide, 2.5 mL (2.7 g, 27.6 mmol) of trimethylsilyl acetylene and 6 mL of triethylamine (heated at 75° C.). The reaction proceeded slowly and after 3 days of heating, an additional 2.5 mL (27.6 mmol) of trimethylsilyl acetylene and 406 mg (0.6 mmol) of bis (triphenylphosphine)palladium (II) chloride was added to the sealed tube (careful to keep the contents under a positive stream of argon) and the resultant mixture heated for 3 additional days (6 days total). Purification by flash chromatography (silica, 5–10% ethyl acetate in hexane) gave crude 2-methoxymethoxy-5-trimethylsilanylethynyl acetophenone. Employing the same general procedure as for the preparation of 5-ethynyl-2-methoxyacetophenone (Compound E1), the crude TMS-acetylene derivative was then converted to 5-ethynyl-2-methoxymethoxy acetophenone using 104 mg (0.75 mmol) of $K_2CO_3$ and 10 mL of methanol, and was isolated by flash chromatography (silica, 5% ethyl acetate in hexane) in >80% purity. Employing the same general procedure as for the preparation of ethyl 4-[(3'-acetyl-4'-methoxy)phenylethynyl]benzoate (Compound 1), the crude acetylene was converted into the title compound using 277 mg (1.0 mmol) of ethyl 4-iodobenzoate (Compound A), 137 mg (0.2 mmol) of bis(triphenylphosphine)palladium (II) chloride, 36 mg (0.2 mmol) of cuprous iodide and 6 mL of triethylamine. Purification by flash chromatography (silica, 10–20% ethyl acetate in hexane) gave the title compound as a white solid.

PMR ($CDCl_3$): δ 1.41 (3H, t, J=7.2 Hz), 2.65 (3H, s), 3.53 (3H, s), 4.37 (2H, t, J=7.2 Hz), 4.38 (2H, q, J=7.1 Hz), 5.32 (2H, s), 7.20 (1H, d, J=8.7 Hz), 7.56 (2H, d, J=8.4 Hz), 7.60 (1H, dd, J=2.2, 8.7 Hz), 7.91 (1H, d, J=2.2 Hz), 8.03 (2H, d, J=8.4 Hz).

Ethyl 4-[[4'-heptyloxy-3'-(1-p-tolyl)vinyl] phenylethynyl]benzoate (Compound 15)

Ethyl 4-[(3'-acetyl-4'-methoxymethoxy)phenylethynyl] benzoate (Compound 14) was converted in a step-wise set of reaction conditions resulting in the final isolation of the title compound as a white solid. Employing the same general procedure as for the preparation of ethyl 4-[[4'-methoxy-3'-(1-hydroxy-1-p-tolyl)ethyl]phenylethynyl]benzoate (Compound 10), 0.4 mL (0.4 mmol) of p-tolylmagnesium bromide (1M in ethyl ether) was used to convert a solution of 100 mg (0.3 mmol) of ethyl 4-[(3'-acetyl-4'-methoxymethoxy)phenylethynyl]benzoate (Compound 14) in 3 mL of tetrahydrofuran into a 3:2 mixture of ethyl 4-[[4'-methoxymethoxy-3'-(1-hydroxy-1-p-tolyl)ethyl] phenylethynyl]benzoate and ethyl 4-[[4'-hydroxy-3'-(1-hydroxy-1-p-tolyl)ethyl]phenylethynyl]benzoate following flash chromatography (silica, 15% ethyl acetate in hexane). To a yellow solution of the crude mixture in 3 mL of ethanol (under a blanket of argon) was added 1 mL of 10% HCl (aq.) solution. The resultant reaction mixture was stirred at ambient temperature for 6.5 hours, heated at 55° C. overnight and quenched with water followed by sat. $NaHCO_3$ (aq.) solution. The resultant mixture was extracted into ethyl acetate and the layers were separated. The organic phase was washed with water and brine, dried over $MgSO_4$, filtered and concentrated in vacuo to a yellow residue. Purification by flash chromatography (silica, 50% ethyl acetate in hexane) gave crude ethyl 4-[[4'-hydroxy-3'-(1-p-tolyl)vinyl] phenylethynyl]benzoate. The crude material was converted into the title compound using the same general procedure as for the preparation of 4-bromo-1-methoxy-3-methylbenzene (Compound E), except using 30 mg (0.2 mmol) of potassium carbonate, 0.025 mL (32 mg, 0.1 mmol) of n-heptyl iodide and 5 mL of acetone. After stirring at ambient temperature for 22 hours, the reaction mixture was concentrated in vacuo and purified by flash chromatography (silica, 5% ethyl acetate in hexane) to give the title compound as a white solid.

PMR ($CDCl_3$): δ 0.87 (3H, t, J=7.3 Hz), 0.95–1.02 (2H, m), 1.08–1.30 (6H, m), 1.34–1.40 (5H, m), 2.33 (3H, s), 3.80 (2H, t, J=7.1 Hz), 4.38 (2H, q, J=7.1 Hz), 5.28 (1H, d, J=1.5 Hz), 5.63 (1H, d, J=1.5 Hz), 6.83 (1H, d, J=9.0 Hz), 7.07 (2H, d, J=8.2 Hz), 7.17 (2H, d, J=8.2 Hz), 7.47–7.52 (2H, m), 7.56 (2H, d, J=8.4 Hz), 8.01 (2H, d, J=8.4 Hz).

4-[[4'-Heptyloxy-3'-(1-p-tolyl)vinyl]phenylethynyl] benzoic acid (Compound 16)

Employing the same general procedure as for the preparation of 4-[[4'-hydroxy-3 '-(4"-methyl)benzoyl] phenylethynyl]benzoic acid (Compound 5), 8.5 mg (0.02 mmol) of ethyl 4-[[4'-heptyloxy-3'-(1-p-tolyl)vinyl] phenylethynyl]benzoate (Compound 15) was converted into the title compound (white solid) using 0.2 mL (0.2 mmol) of NaOH solution (1M in water), 0.8 mL of ethanol and 0.2 mL of tetrahydrofuran. The white solid obtained was rinsed with 1 mL of 10% ethyl acetate in hexane to give the title compound.

PMR ($CDCl_3$): δ 0.86 (3H, t, J=7.2 Hz), 0.90–1.45 (10H, m), 2.31 (3H, s), 3.87 (2H, t, J=6.1 Hz), 5.26 (1H, br s), 5.65 (1H, br s), 7.03 (1H, d, J=8.5 Hz), 7.11 (2H, d, J=8.3 Hz), 7.16 (2H, d, J=8.3 Hz), 7.45 (1H, d, J=2.1 Hz), 7.56 (1H, dd, J=2.1, 8.5 Hz), 7.65 (2H, d, J=8.4 Hz), 8.05 (2H, d, J=8.4 Hz).

Ethyl 4-[(3'-acetyl)phenylethynyl]benzoate (Compound 17)

Employing the same general procedure as for the preparation of ethyl 4-[(3'-acetyl-4'-methoxy)phenylethynyl] benzoate (Compound 1), 600 mg (4.2 mmol) of 3-ethynylacetophenone (Compound K1) was converted into the title compound using 1.3 g (4.6 mmol) of ethyl 4-iodobenzoate (Compound A), 585 mg (0.8 mmol) of bis(triphenylphosphine)palladium (II) chloride, 156 mg (0.8 mmol) of cuprous iodide and 16 mL of triethylamine. Purification by flash chromatography (silica, 10% ethyl acetate in hexane) gave the title compound as a yellow solid.

PMR ($CDCl_3$): δ 1.40 (3H, t, J=7.1 Hz), 2.62 (3H, s), 4.38 (2H, q, J=7.1 Hz), 7.44–7.51 (2H, m), 7.59 (2H, d, J=8.3 Hz), 7.69–7.75 (1H, m), 7.91–7.97 (1H, m), 8.03 (2H, d, J=8.3 Hz), 8.10–8.14 (1H, m).

Ethyl 4-[[3'-(1-hydroxy-1-p-tolyl)ethyl] phenylethynyl]benzoate (Compound 18)

To a cold solution (0° C.) of 112 mg (0.4 mmol) of ethyl 4-[(3'-acetyl)phenylethynyl]benzoate (Compound 17) in 3 mL of tetrahydrofuran (under a blanket of argon) was added 0.6 mL (0.6 mmol) of p-tolylmagnesium bromide (1M in ethyl ether). The solution immediately turned orange and was stirred at 0° C. for 3 hours at which time an additional 0.3 mL (0.3 mmol) of p-tolylmagnesium bromide (1M in ethyl ether ) was added. The reaction mixture was stirred at 0° C. for an additonal 15 minutes, quenched by adding sat. $NH_4Cl$ (aq.) solution and extracted into ethyl acetate. The layers were separated and the organic phase was washed with water and brine, dried over $MgSO_4$, filtered and concentrated in vacuo to a yellow oil. Purification by flash chromatography (silica, 5–10% ethyl acetate in hexane) gave the title compound as a clear film.

PMR ($CDCl_3$): δ 1.40 (3H, t, J=7.1 Hz), 1.95 (3H, s), 2.24 (1H, s), 2.33 (3H, s), 4.38 (2H, q, J=7.1 Hz), 7.14 (2H, d, J=7.9 Hz), 7.25–7.33 (3H, m), 7.39–7.43 (2H, m), 7.56 (2H, d, J=8.5 Hz), 7.63–7.65 (1H, m), 8.01 (2H, d, J=8.5 Hz).

Ethyl 4-[[3'-(1-p-tolyli)vinyl]phenylethynyl] benzoate (Compound 19)

Employing the same general procedure as for the preparation of ethyl 4-[[4'-methoxy-3'-(1-p-tolyl)vinyl]

phenylethynyl]benzoate (Compound 11), 47 mg (0.1 mmol) of ethyl 4-[[3'-(1-hydroxy-1-p-tolyl)ethyl]phenylethynyl] benzoate (Compound 18) was converted into the title compound using 8.5 mg of p-toluene sulfonic acid monohydrate and 2 mL of toluene. Purification by flash chromatography (silica, 10% ethyl acetate in hexane) gave the title compound as a white solid.

PMR (CDCl$_3$): δ 1.40 (3H, t, J=7.1 Hz), 2.37 (3H, s), 4.38 (2H, q, J=7.1 Hz), 5.43 (1H, d, J=1.1 Hz), 5.47 (1H, br s), 7.16 (2H, d, J=8.2 Hz), 7.23 (2H, d, J=8.2 Hz), 7.32–7.35 (2H, m), 7.47–7.51 (1H, m), 7.53–7.60 (3H, m), 8.01 (2H, d, J=8.4 Hz).

4-[[3'-(1-p-Tolyl)vinyl]phenylethynyl]benzoic acid (Compound 20)

Employing the same general procedure as for the preparation of 4-[[4'-hydroxy-3'-(4"-methyl)benzoyl] phenylethynyl]benzoic acid (Compound 5), 36 mg (0.1 mmol) of ethyl 4-[[3'-(1-p-tolyl)vinyl]phenylethynyl] benzoate (Compound 19) was converted into the title compound (white solid) using 1.0 mL (1.0 mmol) of NaOH solution (1M in water), 4.0 mL of ethanol and 0.5 mL of tetrahydrofuran.

PMR (DMSO-d$_6$): δ 2.33 (3H, s), 5.50–5.54 (2H, m), 7.19–7.23 (4H, br s), (1H, d, J=1.1 Hz), 5.47 (1H, br s), 7.19–7.22 (4H, m), 7.36–7.40 (1H, m), 7.44–7.50 (2H, m), 7.56–7.61 (1H, m), 7.67 (2H, d, J=8.5 Hz), 7.96 (2H, d, J=8.5 Hz).

Ethyl 4-[[4'-methoxy-3'-(4"-methyl)benzoyl] phenylethynyl]benzoate (Compound 21)

Employing the same general procedure as for the preparation of ethyl 4-[(3'-acetyl-4'-methoxymethoxy) phenylethynyl]benzoate (Compound 14), a crude sample of 5-bromo-2-methoxy-4'-methylbenzophenone (Compound H) was converted into the title compound (white needles) in a series of reactions. A crude sample (approximately 50% purity) of approximately 195 mg (0.6 mmol) of 5-bromo-2-methoxy-4'-methylbenzophenone (Compound H) was converted into crude 2-methoxy-5-trimethylsilanylethynyl-4'-methylbenzophenone using 112 mg (0.2 mmol) of bis (triphenylphosphine)palladium (II) chloride, 30 mg (0.2 mmol) of cuprous iodide, 0.7 mL (0.6 g, 6.4 mmol) of trimethylsilyl acetylene 10 mL of triethylamine (heated at 75° C.). After purification by flash chromatography (silica, 3% ethyl acetate in hexane), the crude TMS-acetylene derivative obtained was converted into crude 5-ethynyl-2-methoxy-4'-methylbenzophenone using 10 mg (0.07 mmol) of K$_2$CO$_3$ and 10 mL of methanol. Purification by flash chromatography (silica, 5% ethyl acetate in hexane) gave the acetylene derivative in >90% purity. The crude acetylene was converted into the title compound using 86 mg (0.3 mmol) of ethyl 4-iodobenzoate (Compound A), 50 mg (0.07 mmol) of bis(triphenylphosphine)palladium (II) chloride, 13 mg (0.07 mmol) of cuprous iodide and 6 mL of triethylamine. Purification by flash chromatography (silica, 15% ethyl acetate in hexane) followed by recrystallization from methanol gave the title compound as white needles.

PMR (CDCl$_3$): δ 1.40 (3H, t, J=7.1 Hz), 2.43 (3H, s), 3.78 (3H, s), 6.99 (1H, d, J=8.7 Hz), 7.25 (2H, d, J=8 Hz), 7.52 (1H, d, J=2.1 Hz), 7.54 (2H, d, J=8.4 Hz), 7.64 (1H, dd, J=2.1, 8.7 Hz), 7.73 (2H, d, J=8.3 Hz), 8.01 (2H, d, J=8.3 Hz).

4-[[4'-methoxy-3'-(4"-methyl)benzoyl] phenylethynyl]benzoic acid (Compound 22)

Employing the same general procedure as for the preparation 4-[(3'-acetyl-4'-methoxy)phenylethynyl]benzoic acid (Compound 2), 46 mg (0.1 mmol) ethyl 4-[[4'-methoxy-3'-(4"-methyl)benzoyl]phenylethynyl]benzoate (Compound 21) was converted into the title compound (white solid) using 1.2 mL (1.2 mmol) of LiOH solution (1M in water) and 5 mL of tetrahydrofuran. The white solid obtained was rinsed with 3 mL of 5% ethyl acetate in hexane to give the title compound.

PMR (Aceton-d$_6$): δ 2.38 (3H, s), 3.73 (3H, s), 7.26 (1H, d, J=8.8 Hz), 7.33 (2H, d, J=7.8 Hz), 7.50 (1H, d, J=2.1 Hz), 7.59–7.65 (4H, m), 7.60 (1H, dd, J=2.1, 8.6 Hz), 7.94 (2H, d, J=8.6 Hz).

Ethyl 4-[[4'-methoxymethoxy-2'-methyl-5'-(4"-methyl)benzoyl]phenylethynyl]-2-fluoro-benzoate (Compound 23)

Employing the same general procedure as for the preparation of ethyl 4-[(3'-acetyl-4'-methoxy)phenylethynyl] benzoate (Compound 1), 123 mg (0.4 mmol) of 5-ethynyl-4-methyl-2-methoxymethoxy-4'-methylbenzophenone (Compound L1) was converted into the title compound using 136 mg (0.5 mmol) of ethyl 2-fluoro-4-iodobenzoate (Compound C), 74 mg (0.1 mmol) of bis (triphenylphosphine)palladium (II) chloride, 20 mg (0.1 mmol) of cuprous iodide and 5.0 mL of a 4:1 mixture of triethylamine:N,N-dimethylformamide. Purification by flash chromatography (silica, 10% ethyl acetate in hexane) gave the title compound as a yellow solid.

PMR (CDCl$_3$): δ 1.40 (3H, t, J=7.1 Hz), 2.42 (3H, s), 2.56 (3H, s), 3.34 (3H, s), 4.40 (2H, q, J=7.1 Hz), 5.09 (2H, s), 7.11 (1H, s), 7.20–7.35 (4H, m), 7.51 (1H, s), 7.73 (2H, d, J=8.2 Hz), 7.90 (1H, t, J=7.9 Hz, J (C-F)=7.9 Hz).

Ethyl 4-[[4'-hydroxy-2'-methyl-5'-(4"-methyl) benzoyl]phenylethynyl]- 2-fluoro-benzoate (Compound 24)

Employing the same general procedure as for the preparation of ethyl 4-[[4'-hydroxy-3'-(4"-methyl)benzoyl] phenylethynyl]benzoate (Compound 4), 13 mg (0.03 mmol) of ethyl 4-[[4'-methoxymethoxy-2'-methyl-5'-(4"-methyl) benzoyl]phenylethynyl]-2-fluoro-benzoate (Compound 23) was converted into the title compound (yellow oil) using 1 drop of c. HCl and and 2 mL of ethanol. Purification by flash chromatography (silica, 10% ethyl acetate in hexane) gave the title compound as a yellow oil.

PMR (CDCl$_3$): δ 1.40 (3H, t, J=7.1 Hz), 2.47 (3H, s), 2.53 (3H, s), 4.39 (2H, q, J=7.1 Hz), 6.97 (1H, s), 7.22 (1H, dd, J=1.5 Hz, J (C-F)=9.1 Hz), 7.31 (1H, dd, J=1.5, 8.1 Hz), 7.35 (2H, d, J=8.1 Hz), 7.62 (2H, d, J=8.1 Hz), 7.78 (1H, s), 7.89 (1H, t, J=7.9 Hz, J (C-F)=7.8 Hz), 12.27 (1H, s).

4-[[4'-Hydroxy-2'-methyl-5'-(4"-methyl)benzoyl] phenylethynyl]-2-fluoro-benzoic acid (Compound 25)

Employing the same general procedure as for the preparation of 4-[[4'-hydroxy-3'-(4"-methyl)benzoyl] phenylethynyl]benzoic acid (Compound 5), 10 mg (0.025 mmol) of ethyl 4-[[4'-hydroxy-2'-methyl-5'-(4"-methyl) benzoyl]phenylethynyl]-2-fluoro-benzoate (Compound 24) was converted into the title compound (yellow crystals) using 0.25 mL (0.25 mmol) of NaOH solution (1M in water), 1.0 mL of ethanol and 0.2 mL of tetrahydrofuran. Recrystallization from acetonitrile gave the title compound as yellow needles.

PMR (Aceton-d$_6$): δ 2.46 (3H, s), 2.57 (3H, s), 7.04 (1H, s), 7.37–7.46 (4H, m) 7.80 (1H, s), 7.62–7.70 (2H, d, J=8.3 Hz), 7.96 (1H, t, J=7.5 Hz, J (C-F)=8.0 Hz).

Ethyl 4-[[4'-isopropoxy-3'-(1-p-tolyl)vinyl]pheynlethynyl]benzoate (Compound 26)

Employing the same general procedure as for the preparation of ethyl 4-[(3'-acetyl-4'-methoxy)phenylethynyl]benzoate (Compound 1), 20 mg (0.07 mmol) 4-ethynyl-1-isopropoxy-2-[(1-p-tolyl)vinyl]benzene (Compound M1) was converted into the title compound using 24 mg (0.09 mmol) of ethyl 4-iodobenzoate (Compound A), 13 mg (0.02 mmol) of bis(triphenylphosphine)palladium (II) chloride, 4 mg (0.02 mmol) of cuprous iodide and 3.5 mL of triethylamine. Purification by flash chromatography (silica, 5% ethyl acetate in hexane) gave the title compound as a white solid.

PMR (CDCl$_3$): δ 1.00 (6H, d, J=6.0 Hz), 1.40 (3H, t, J=7.0 Hz), 2.34 (3H, s), 4.32–4.44 (3H, m), 5.29 (1H, d, J=1.4 Hz), 5.60 (1H, br s), 6.85 (1H, d, J=8.2 Hz), 7.08 (2H, d, J=8.2 Hz), 7.16 (2H, d, J=8.2 Hz), 7.45–7.52 (2H, m), 7.56 (2H, d, J=8.4 Hz), 8.01 (2H, d, J=8.4 Hz).

Ethyl 4-[[4'-isopropoxy-3'-(1-p-tolyl)vinyl]phenylethynyl]-2-fluoro-benzoate (Compound 27)

Employing the same general procedure as for the preparation of ethyl 4-[(3'-acetyl-4'-methoxy)phenylethynyl]benzoate (Compound 1), 16 mg (0.06 mmol) 4-ethynyl-1-isopropoxy-2-[(1-p-tolyl)vinyl]benzene (Compound M1) was converted into the title compound using 17.5 mg (0.06 mmol) of ethyl 2-fluoro-4-iodobenzoate (Compound C), 10 mg (0.015 mmol) of bis(triphenylphosphine)palladium (II) chloride, 3.2 mg (0.02 mmol) of cuprous iodide and 3.5 mL of triethylamine. Purification by flash chromatography (silica, 5% ethyl acetate in hexane) gave the title compound as a yellow oil which later solidified to a yellow solid.

PMR (CDCl$_3$): δ 1.00 (6H, d, J=6.0 Hz), 1.40 (3H, t, J=7.1 Hz), 2.34 (3H, s), 4.3–4.5 (3H, m), 5.28 (1H, d, J=1.4 Hz), 5.60 (1H, d, J=1.4 Hz), 6.85 (1H, d, J=8.3 Hz), 7.08 (2H, d, J=8.1 Hz), 7.15 (2H, d, J=8.1 Hz), 7.25 (1H, dd, J=1.5 Hz, J (C-F)=11.4 Hz), 7.31 (1H, dd, J=1.5, 8.1 Hz), 7.44–7.50 (2H, m), 7.90 (1H, t, J=7.9 Hz, J (C-F)=7.8 Hz).

4-[[4'-Isopropoxy-3'-(1-p-tolyl)vinyl]phenylethynyl]benzoic acid (Compound 28)

Employing the same general procedure as for the preparation of 4-[[4'-hydroxy-3'-(4"-methyl)benzoyl]phenylethynyl]benzoic acid (Compound 5), 17 mg (0.04 mmol) of ethyl 4-[[4'-isopropoxy-3'-(1-p-tolyl)vinyl]phenylethynyl]benzoate (Compound 26) was converted into the title compound (white crystals) using 0.4 mL (0.4 mmol) of NaOH solution (1M in water), 1.6 mL of ethanol and 0.4 mL of tetrahydrofuran. Recrystallization from acetonitrile gave the title compound as white crystals.

PMR (Aceton-d$_6$): δ 0.99 (6H, d, J=6.0 Hz), 2.31 (3H, s), 4.54 (1H, heptet, J=6.0 Hz), 5.24 (1H, d, J=1.5 Hz), 5.61 (1H, d, J=1.5 Hz), 7.05 (1H, d, J=8.5 Hz), 7.07–7.20 (4H, m), 7.43 (1H, d, J=2.2 Hz), 7.54 (1H, dd, J=2.2, 8.4 Hz), 7.64 (2H, d, J=8.5 Hz), 8.04 (2H, d, J=8.5 Hz).

4-[[4'-Isopropoxy-3'-(1-p-tolyl)vinyl]phenylethynyl]-2-fluoro-benzoic acid (Compound 29)

Employing the same general procedure as for the preparation of 4-[[4'-hydroxy-3'-(4"-methyl)benzoyl]phenylethynyl]benzoic acid (Compound 5), 10 mg (0.02 mmol) of ethyl 4-[[4'-isopropoxy-3'-(1-p-tolyl)vinyl]phenylethynyl]-2-fluoro-benzoate (Compound 27) was converted into the title compound (white solid) using 0.2 mL (0.2 mmol) of NaOH solution (1M in water), 1.0 mL of ethanol and 0.2 mL of tetrahydrofuran. The white solid obtained was rinsed with a small amount of 5% ethyl acetate in hexane to give the title compound.

PMR (Aceton-d$_6$): δ 0.99 (6H, d, J=6.0 Hz), 2.31 (3H, s), 4.55 (1H, heptet, J=6.0 Hz), 5.24 (1H, br s), 5.62 (1H, d, J=1.6 Hz), 7.03–7.20 (5H, m), 7.36–7.60 (3H, m), 7.55 (1H, dd, J=2.2, 8.5 Hz), 7.97 (1H, t, J=8.0 Hz, J (C-F)=7.8 Hz).

Ethyl 4-[[4'-isopropoxy-3'-(1-m-tolyl)vinyl]phenylethynyl]benzoate (Compound 30)

Employing the same general procedure as for the preparation of ethyl 4-[(3'-acetyl-4'-methoxy)phenylethynyl]benzoate (Compound 1), 14 mg (0.05 mmol) of 4-ethynyl-1-isopropoxy-2-[(1-m-tolyl)vinyl]benzene (Compound N1) was converted into the title compound using 14 mg (0.04 mmol) of ethyl 4-iodobenzoate (Compound A), 9 mg (0.01 mmol) of bis(triphenylphosphine)palladium (II) chloride, 2 mg (0.01 mmol) of cuprous iodide and 3 mL of triethylamine. Purification by flash chromatography (silica, 1% ethyl acetate in hexane) gave the title compound as a clear oil which later solidified to a white solid.

PMR (CDCl$_3$): δ 0.99 (6H, d, J=6.0 Hz), 1.40 (3H, t, J=7.1 Hz), 2.30 (3H, s), 4.33–4.46 (3H, m), 5.32 (1H, d, J=1.5 Hz), 5.61 (1H, br s), 6.84 (1H, d, J=8.4 Hz), 7.05–7.20 (4H, m), 7.45–7.52 (2H, m), 7.57 (2H, d, J=8.4 Hz), 8.02 (2H, d, J=8.4 Hz).

4-[[4'-Isopropoxy-3'-(1-m-tolyl)vinyl]phenylethynyl]benzoic acid (Compound 31)

Employing the same general procedure as for the preparation of 4-[[4'-hydroxy-3 '-(4"-methyl)benzoyl]phenylethynyl]benzoic acid (Compound 5), 10 mg (0.02 mmol) of ethyl 4-[[4'-isopropoxy-3'-(1-m-tolyl)vinyl]phenylethynyl]benzoate (Compound 30) was converted into the title compound (white solid) using 0.3 mL (0.3 mmol) of NaOH solution (1M in water), 1.2 mL of ethanol and 0.3 mL of tetrahydrofuran. The white solid obtained was rinsed with 1.5 mL of 5% ethyl acetate in hexane to give the title compound.

PMR (Aceton-d$_6$): δ 0.97 (6H, d, J=6.0 Hz), 2.28 (3H, s), 4.54 (1H, heptet, J=6.0 Hz), 5.29 (1H, d, J=1.5 Hz), 5.67 (1H, br s), 7.02–7.22 (5H, m), 7.46 (1H, d, J=2.2 Hz), 7.54 (1H, dd, J=2.2, 8.4 Hz), 7.65 (2H, d, J=8.4 Hz), 8.05 (2H, d, J=8.4 Hz).

Ethyl 4-[[4'-tert-butyldimethylsilanyloxy-3'-(1-p-tolyl)vinyl]phenylethynyl]benzoate (Compound 32)

Employing the same general procedure as for the preparation of ethyl 4-[(3'-acetyl-4'-methoxy)phenylethynyl]benzoate (Compound 1), 12 mg (0.04 mmol) of 1-tert-butyldimethylsilanyloxy-4-ethynyl-2-[(1-p-tolyl)vinyl]benzene (Compound O1) was converted into the title compound using 10 mg (0.04 mmol) of ethyl 4-iodobenzoate (Compound A), 6 mg (0.01 mmol) of bis(triphenylphosphine)palladium (II) chloride, 1.5 mg (0.01 mmol) of cuprous iodide and 2 mL of triethylamine. Purification by flash chromatography (silica, 1% ethyl acetate in hexane) gave the title compound as a yellow oil.

PMR (CDCl$_3$): δ 0.07 (6H, s), 0.73 (9H, s), 1.40 (3H, t, J=7.0 Hz), 2.32 (3H, s), 4.38 (2H, q, J=7.0 Hz), 5.25 (1H, d, J=1.2 Hz), 5.71 (1H, d, J=1.2 Hz), 6.80 (1H, d, J=8.2 Hz), 7.08 (2H, d, J=8.4 Hz), 7.18 (2H, d, J=8.4 Hz), 7.38–7.48 (2H, m), 7.55 (2H, d, J=8.2 Hz), 8.01 (2H, d, J=8.2 Hz).

What is claimed is:
1. A compound of the formula

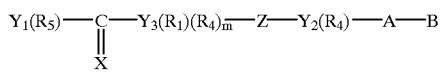

where X is O, S, C($R_2$) or NOR*,
R* is H, $C_{1-6}$ alkyl or phenyl;
$R_1$ is H, lower alkyl of 1 to 10 carbons, F, Cl, Br, I, $CF_3$, $OR_2SR_2$, $OCH_2OC_{1-6}$ alkyl or $CF_2CF_3$;
$R_2$ is independently H, lower alkyl of 1 to 10 carbons, $R_3Si$, or $COR_3$ where $R_3$ is H, lower alkyl of 1 to 6 carbons or phenyl;
$R_4$ is lower alkyl of 1 to 6 carbons, F, Cl, Br, I, $CF_3$, $CF_2CF_3$, $NO_2$, $N(R_6)_2$, CN, $COR_3$, or $N(R_6)$—$COR_3$;
m is an integer between 0 and 3;
$Y_1$ is phenyl, naphthyl or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, $COOC_{1-6}$alkyl; $N_3$; $N(R_6)_2$, OH, $OR_3$; $SR_3$; $OCOR_3$, or $SCOR_3$;
Z is —C≡C—
—N=N—,
—N(O)=N—,
—N=N(O)—,
—N=$CR_6$—,
$CR_6$=N,
—($CR_6$=$CR_6$)$_n$— where n is an integer having the value 0–5,
—CO—$NR_6$—,
—CS—$NR_6$—,
—$NR_6$—CO,
—$NR_6$—CS,
—OCO—;
—CSO—;
—OCS—;
—CO—$CR_6$=$CR_6$—
$R_6$ is independently H or lower alkyl of 1 to 6 carbons;
$Y_2$ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being unsubstituted or substituted with one or two $R_4$ groups, or
when Z is —($CR_6$=$CR_6$)$_n$ and n is 3, 4 or 5 then $Y_2$ represents a direct valence bond between said ($CR_6$=$CR_6$)$_n$ group and B;
$Y_3$ is phenyl, pyridy, thienyl or funyl unsubstituted or substituted with up to 3 $R_1$ groups and unsubstituted or substituted with up ot 3 $R_4$ groups, and
where the A—B group is $(CH_2)_q$COOH or $(CH_2)_q$—$COOR_8$, q is an integer having the values 0 to 5, and $R_8$ is an alkyl group of 1 to 10 carbons or (trimethylsilyl) alkyl where the alkyl group has 1 to 10 carbons, or a cycloalkyl group of 5 to 10 carbons, or $R_8$ is phenyl or lower alkylphenyl.

2. A compound of the formula

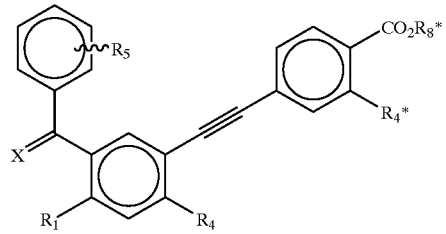

wherein X is O, or $CH_2$;
$R_1$ is H, $OCH_2OCH_3$, or $OR_2$;
$R_2$ is H, lower alkyl of 1 to 10 carbons, tri-($C_{1-6}$alkyl)silyl, or $COR_3$ where $R_3$ is H, or lower alkyl;
$R_4$ is H or lower alkyl of 1 to 6 carbons;
$R_4$* is H or F;
$R_5$ is H, F or lower alkyl of 1 to 6 carbons, and
$R_8$* is H, lower alkyl of 1 to 6 carbons, or a pharmaceutically acceptable salt thereof.

3. A compound in accordance with claim 2 where X is $CH_2$ and $R_5$ is 4-methyl.
4. A compound in accordance with claim 3 where $R_4$ is H.
5. A compound in accordance with claim 4 where $R_1$ is H.
6. A compound in accordance with claim 5 where $R_4$* is H and $R_8$* is H or ethyl.
7. A compound in accordance with claim 4 where $R_1$ is $CH_3COO$.
8. A compound in accordance with claim 7 where $R_4$* is H and $R_8$* is H or ethyl.
9. A compound in accordance with claim 4 where $R_1$ is $CH_3OCH_2O$—.
10. A compound in accordance with claim 9 where $R_4$* is H and $R_8$* is H or ethyl.
11. A compound in accordance with claim 4 where $R_1$ is OH.
12. A compound in accordance with claim 11 where $R_4$* is H and $R_8$* is H or ethyl.
13. A compound in accordance with claim 4 where $R_1$ is $OCH_3$.
14. A compound in accordance with claim 13 where $R_4$* is H and $R_8$* is H or ethyl.
15. A compound in accordance with claim 4 where $R_1$ is O-n-heptyl.
16. A compound in accordance with claim 15 where $R_4$* is H and $R_8$* is H or ethyl.
17. A compound in accordance with claim 4 where $R_1$ is $OCH(CH_3)_2$.
18. A compound in accordance with claim 17 where $R_4$* is H and $R_8$* is H or ethyl.
19. A compound in accordance with claim 4 where $R_1$ is $OSi(CH_3)_2$-t-butyl.
20. A compound in accordance with claim 19 where $R_4$* is H and $R_8$* is H or ethyl.
21. A compound in accordance with claim 17 where $R_4$* is F and $R_8$* is H or ethyl.
22. A compound in accordance with claim 2 where X is $CH_2$ and $R_5$ is 3-methyl.
23. A compound in accordance with claim 22 where $R_4$ is H, $R_1$ is $OCH(CH_3)_2$ $R_4$* is H and $R_8$* is H or ethyl.
24. A compound in accordance with claim 2 where X is O and $R_5$ is 4-methyl.
25. A compound in accordance with claim 24 where $R_4$ is H.

26. A compound in accordance with claim 25 where $R_1$ is $CH_3OCH_2O-$.

27. A compound in accordance with claim 26 where $R_4^*$ is H and $R_8^*$ is H or ethyl.

28. A compound in accordance with claim 25 where $R_1$ is OH.

29. A compound in accordance with claim 28 where $R_4^*$ is H and $R_8^*$ is H or ethyl.

30. A compound in accordance with claim 25 where $R_1$ is $OCH_3$.

31. A compound in accordance with claim 30 where $R_4^*$ is H and $R_8^*$ is H or ethyl.

32. A compound in accordance with claim 24 where $R_4$ is $CH_3$.

33. A compound in accordance with claim 32 where $R_1$ is $CH_3OCH_2O-$.

34. A compound in accordance with claim 33 where $R_4^*$ is F and $R_8^*$ is H or ethyl.

35. A compound in accordance with claim 32 where $R_1$ is OH.

36. A compound in accordance with claim 35 where $R_4^*$ is F and $R_8^*$ is H or ethyl.

* * * * *